United States Patent
Tamura et al.

(10) Patent No.: US 10,288,747 B2
(45) Date of Patent: May 14, 2019

(54) RADIATION DETECTION APPARATUS FOR CHANGING SENSITIVITY OF RADIATION SENSING DURING CONTROL FOR RADIATION IMAGING, METHOD OF CONTROLLING THE SAME, AND NON-TRANSITORY COMPUTER-READABLE STORAGE MEDIUM

(71) Applicant: CANON KABUSHIKI KAISHA, Tokyo (JP)

(72) Inventors: Toshikazu Tamura, Utsunomiya (JP); Taro Hiroike, Yamato (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 28 days.

(21) Appl. No.: 14/750,038

(22) Filed: Jun. 25, 2015

(65) Prior Publication Data

US 2015/0378030 A1   Dec. 31, 2015

(30) Foreign Application Priority Data

Jun. 30, 2014 (JP) ................................. 2014-135167

(51) Int. Cl.
    *G01T 1/17*    (2006.01)
    *H05G 1/44*    (2006.01)
    *G01T 1/02*    (2006.01)
    *G01N 23/04*   (2018.01)
    *A61B 6/00*    (2006.01)
    (Continued)

(52) U.S. Cl.
    CPC ................ *G01T 1/17* (2013.01); *A61B 6/542* (2013.01); *G01N 23/04* (2013.01); *G01T 1/02* (2013.01); *H04N 5/32* (2013.01); *H04N 5/3765* (2013.01); *H05G 1/44* (2013.01)

(58) Field of Classification Search
    None
    See application file for complete search history.

(56) References Cited

U.S. PATENT DOCUMENTS 5,568,530 A * 10/1996 Saito ...................... A61B 6/032
                                                          378/4
9,541,653 B2    1/2017 Iwashita et al.
(Continued)

FOREIGN PATENT DOCUMENTS

CN   102315233 A   1/2012
CN   102388321 A   3/2012
(Continued)

OTHER PUBLICATIONS

European Search Report issued in corresponding application No. 15170850.0 dated Oct. 29, 2015.
(Continued)

*Primary Examiner* — James Choi
(74) *Attorney, Agent, or Firm* — Carter, DeLuca, Farrell & Schmidt, LLP

(57) ABSTRACT

A radiation detection apparatus detects radiation and generates irradiation sensing information corresponding to a dose of detected radiation, senses whether radiation emitted from a radiation generator is detected, based on the generated irradiation sensing information, and receives a control signal from a controller. The apparatus switches detectability for detection of the radiation based on a control signal received from the controller.

20 Claims, 16 Drawing Sheets

(51) Int. Cl.
*H04N 5/376* (2011.01)
*H04N 5/32* (2006.01)

(56) References Cited

U.S. PATENT DOCUMENTS

| | | | |
|---|---|---|---|
| 2002/0050568 A1 | 5/2002 | Nonaka | |
| 2004/0159901 A1* | 8/2004 | Kaifu | G01T 1/2018 257/431 |
| 2007/0116172 A1* | 5/2007 | Hsieh | A61B 6/032 378/8 |
| 2011/0050403 A1* | 3/2011 | Liu | A61B 6/4405 340/384.1 |
| 2011/0095192 A1* | 4/2011 | Johnson | G01T 1/248 250/370.1 |
| 2011/0127415 A1* | 6/2011 | Kanter | G01J 1/44 250/252.1 |
| 2011/0240865 A1* | 10/2011 | Frach | G01T 1/2018 250/362 |
| 2012/0288061 A1 | 11/2012 | Okada | |
| 2013/0313439 A1* | 11/2013 | Okada | H04N 5/32 250/366 |
| 2014/0021365 A1* | 1/2014 | Oda | G01T 1/17 250/395 |

FOREIGN PATENT DOCUMENTS

| | | |
|---|---|---|
| CN | 102780857 A | 11/2012 |
| CN | 102854523 A | 1/2013 |
| CN | 103654808 A | 3/2014 |
| EP | 0757474 A1 | 2/1997 |
| EP | 2403237 A1 | 1/2012 |
| EP | 2702944 A1 | 3/2014 |
| JP | H11155847 A | 6/1999 |
| JP | 2010-264085 A | 11/2010 |
| JP | 4684747 B2 | 5/2011 |
| JP | 2013-051657 A | 3/2013 |
| JP | 2013-141484 A | 7/2013 |
| JP | 2013-232884 A | 11/2013 |

OTHER PUBLICATIONS

Office Action issued in corresponding European application No. 15170850.0 dated Jul. 5, 2017.
Notification of First Office Action for Chinese Appln. No. 201510374186.1 dated Oct. 11, 2017.
Japanese Office Action corresponding to Japanese Appln. No. 2014-135167 dated Apr. 2, 2018, 6 pages.

* cited by examiner

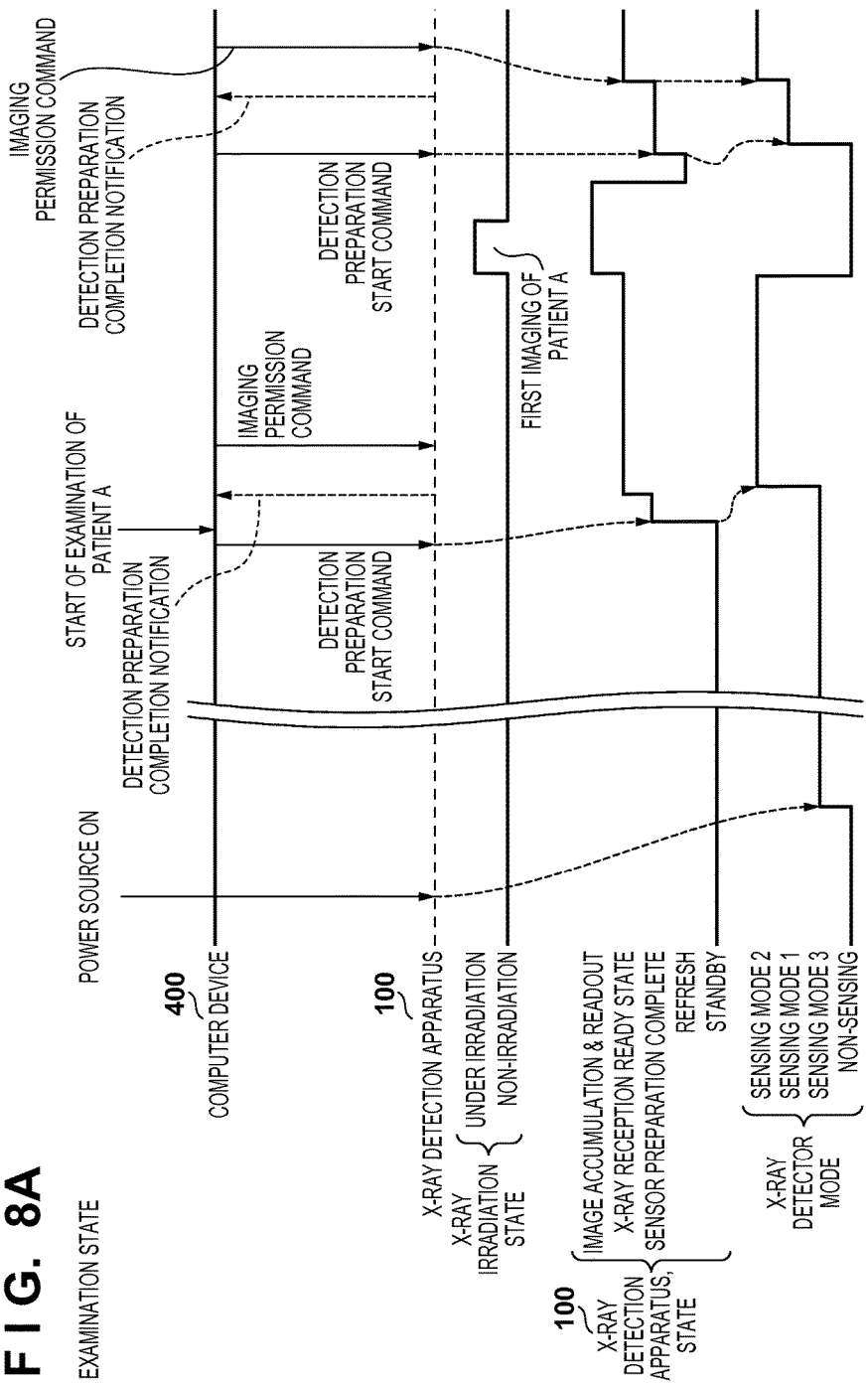

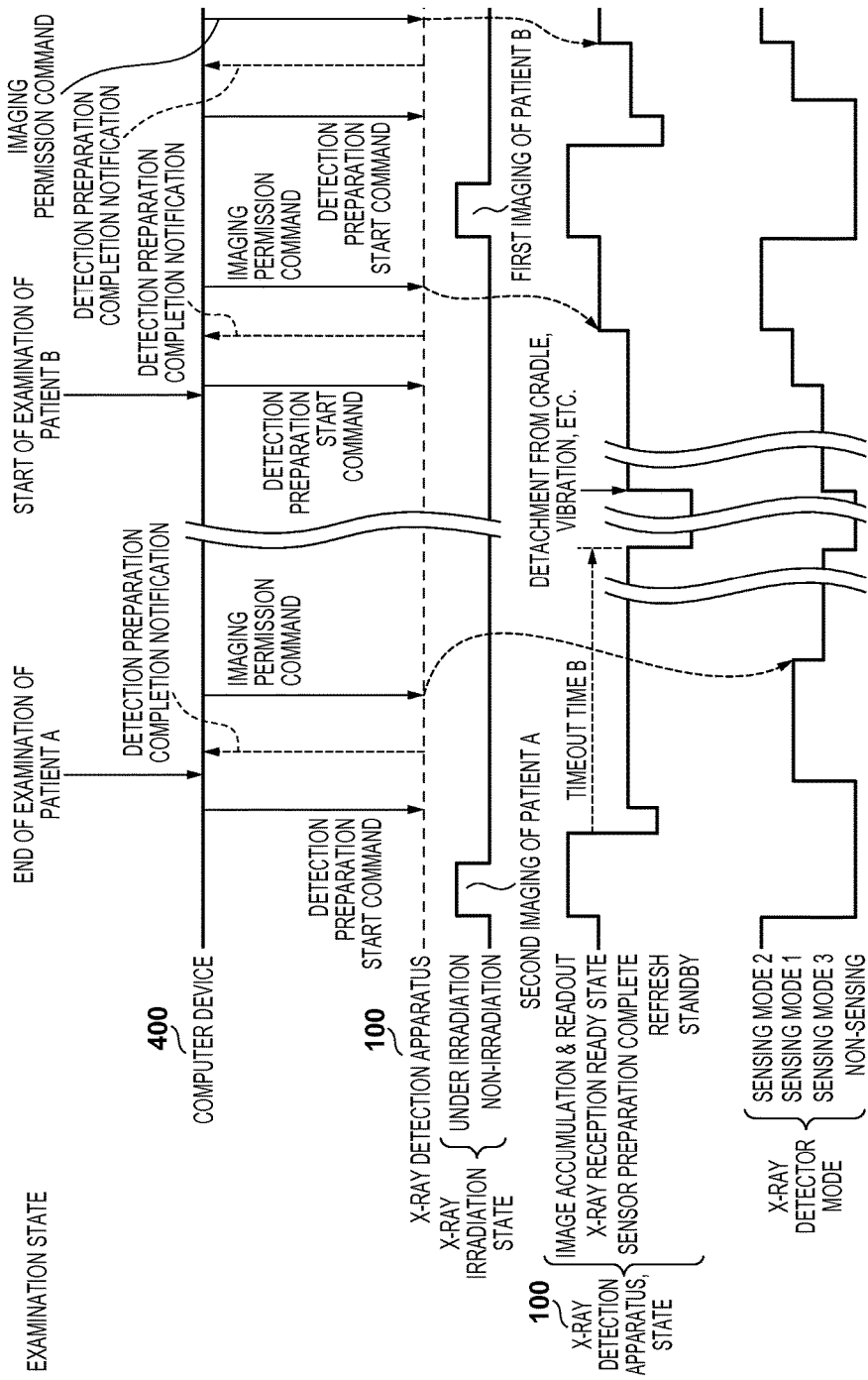

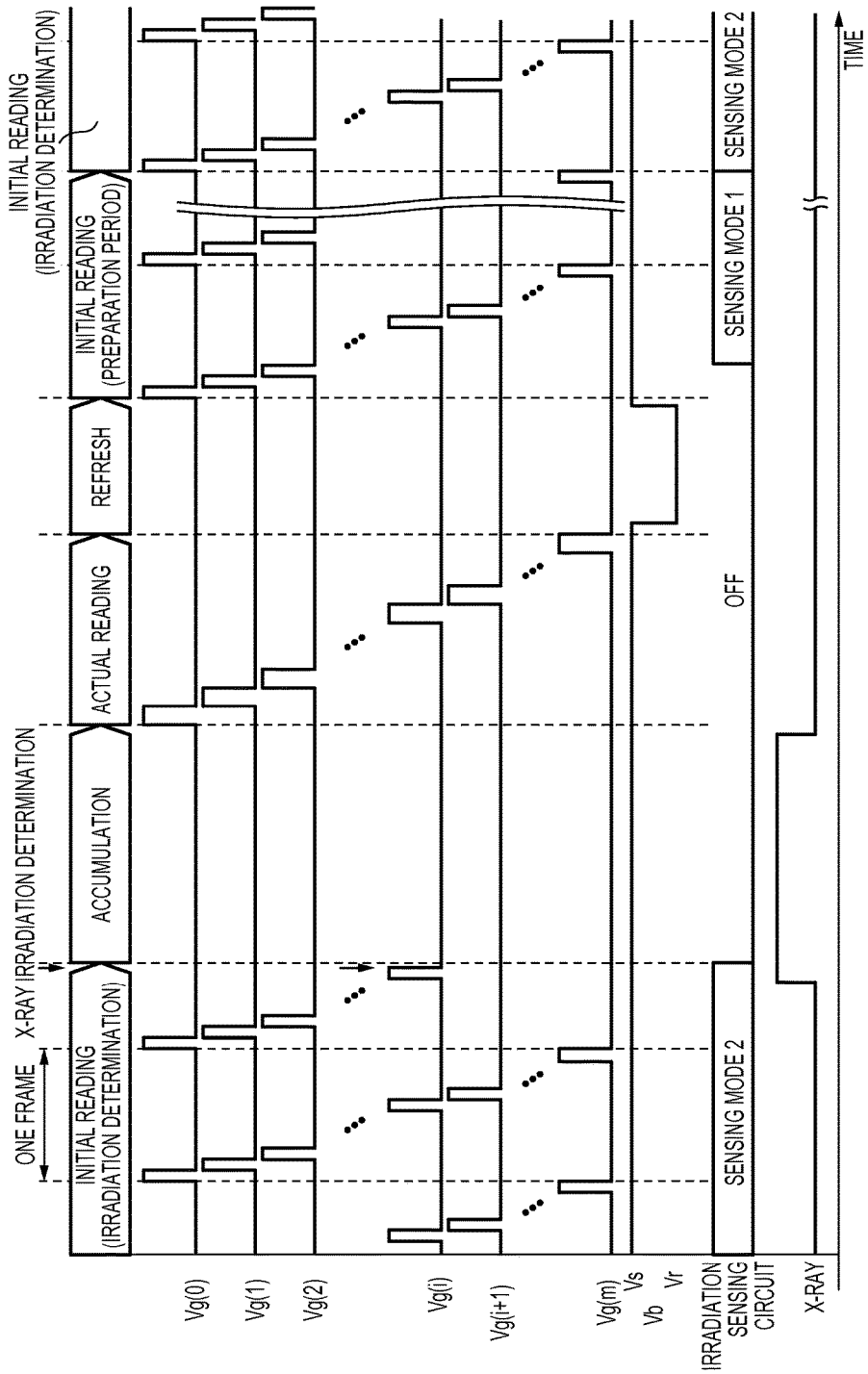

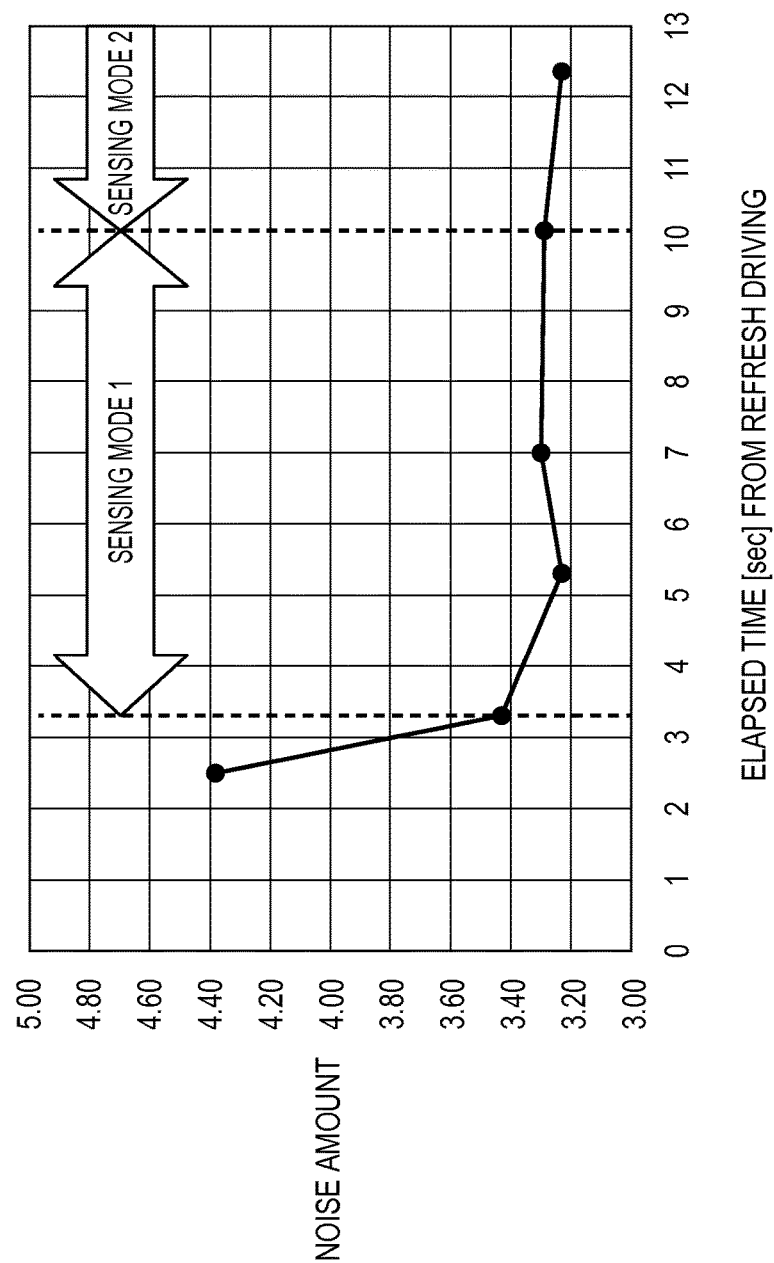

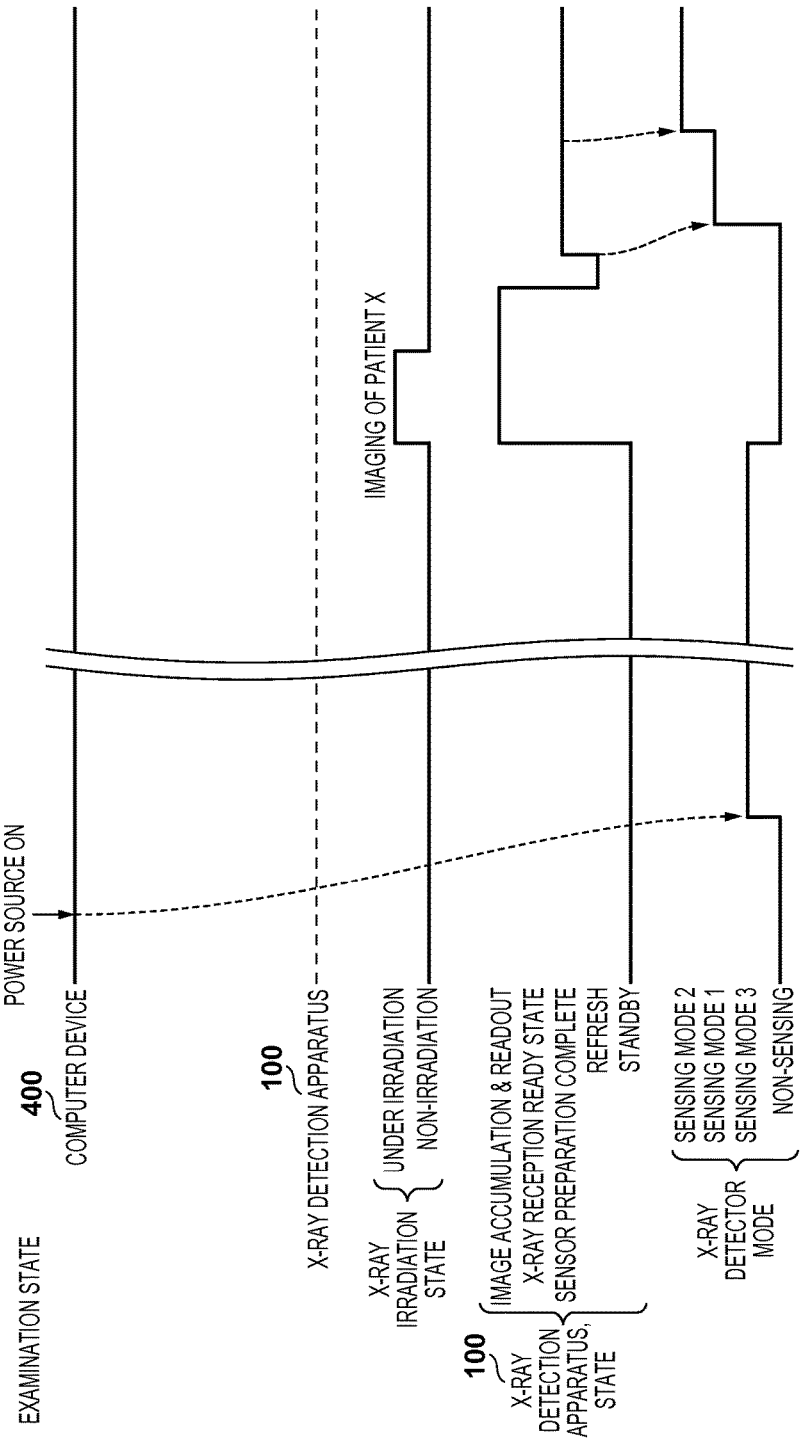

RADIATION DETECTION APPARATUS FOR CHANGING SENSITIVITY OF RADIATION SENSING DURING CONTROL FOR RADIATION IMAGING, METHOD OF CONTROLLING THE SAME, AND NON-TRANSITORY COMPUTER-READABLE STORAGE MEDIUM

BACKGROUND OF THE INVENTION

Field of the Invention

The present invention relates to a radiation detection technique and, more particularly, to a radiation detection apparatus which can obtain an X-ray image without exchanging any synchronization signal with a radiation generator, a method of controlling the same, and a non-transitory computer-readable storage medium.

Description of the Related Art

Recently, the digitization of radiation images such as X-ray images has been promoted in the medical field, leading to many merits. For example, it is possible to speed up diagnosis by allowing a user to quickly check obtained images on a display device or the like upon digital transmission to it. In addition, digitization improves diagnosis accuracy with respect to a fine lesion as well as automating diagnosis by various types of image processing. Furthermore, since there is no need to secure a film storage space, the space efficiency inside a hospital greatly improves. Moreover, since digital transmission hardly suffers deterioration in data, it is possible to transmit obtained images to a remote place without any deterioration. Making the most of these features can receive diagnosis from a highly trained doctor by transmitting images obtained in a home care site, a disaster site, or the like to a fully-equipped urban hospital.

Radiation imaging apparatuses have been commercially available and are rapidly popular, which use a digital radiography method of forming an image by converting radiation into an electric signal by using a plurality of radiation detecting elements arrayed in a two-dimensional matrix instead of a film. As a radiation imaging apparatus of this type, an X-ray detection apparatus using an FPD (Flat Panel Detector) has been proposed. In such an X-ray detection apparatus, minute X-ray detectors, each obtained by stacking a solid-state photoelectric conversion element and a scintillator which converts X-rays into visible light, are arranged, as image sensing elements, in a two-dimensional matrix, and each image sensing element converts irradiated X-rays with which an object is irradiated into an electric signal (charge amount) corresponding to the dose of irradiation. In general, an FPD can accumulate the charges, generated by X-ray irradiation, in solid-state photoelectric conversion elements by controlling a voltage to be applied to the elements. Thereafter, the FPD reads out charges from the solid-state photoelectric conversion elements by controlling the voltage to be applied to another voltage, and forms image data in accordance with the accumulated charge amounts.

When obtaining an X-ray image by using the FPD, it is necessary, in consideration of the characteristics of the solid-state photoelectric conversion elements in use, to accurately synchronize the timing of X-ray irradiation with the timing when the detectors accumulate charges (imaging). For this reason, as disclosed in, for example, Japanese Patent No 4684747, there has been proposed an X-ray imaging system which synchronizes X-ray irradiation with the timing of imaging exchanging synchronization signals between the X-ray generator and the FPD. More specifically, the FPD makes preparation for imaging in response to an irradiation request signal from the X-ray generator, and an irradiation permission signal is transmitted to the X-ray generator in accordance with the start of imaging by the FPD (the start of the accumulation of charges), thereby irradiating an object with X-rays. In the X-ray imaging system proposed in Japanese Patent Laid-Open No. 11-155847, the FPD detects the timing of X-ray irradiation by detecting a change in current caused inside upon X-ray irradiation, and starts imaging in response to the detection as a trigger, thereby establishing synchronization between X-ray irradiation and the timing of imaging.

In a system in which the X-ray generator and the X-ray detection apparatus mutually exchange no synchronization signals, the X-ray generator can generate X-rays regardless of whether the X-ray detection apparatus is ready for imaging. In this case, X-ray irradiation greatly changes the state of the X-ray detection apparatus. This influences the image to be obtained by the next imaging operation unless proper processing is performed. In order to reduce this influence, the X-ray detection apparatus may always detect the start of X-ray irradiation even before the completion of preparation for imaging as well as after the completion of preparation for imaging.

However, there are increasing cases in which since weak signals are handled for the detection or the start of X-ray irradiation, when the X-ray detection apparatus is always ready for the detection of X-rays, the apparatus erroneously detects, as imaging, an event which is not imaging because of external electromagnetic wave noise or impact. The cycle time deteriorates due to a detection error or the operation load for the restoration from a detection error increases. This leads to deterioration in the efficiency of imaging. In addition, even if noise resistance is ensured, the power consumption increases.

SUMMARY OF THE INVENTION

According to one aspect of the present invention, there is a provided a radiation detection apparatus which comprises a detection unit configured to detect radiation and generate irradiation sensing information corresponding to a dose of detected radiation, a sensing unit configured to sense whether radiation emitted from a radiation generator is detected, based on the irradiation sensing information generated by the detection unit, and a communication unit configured to receive a control signal from a controller, wherein the sensing unit switches detectability for detection of the radiation based on a control signal received from the controller via the communication unit.

Further features of the present invention will become apparent from the following description of exemplary embodiments (with reference to the attached drawings).

BRIEF DESCRIPTION OF THE DRAWINGS

FIGS. 8A to 8C are timing charts for overall X-ray examination processing;

FIG. 9 is a timing chart showing the driving timing of an X-ray detector;

FIG. 10 is a graph representing a temporal change in noise in current information;

FIG. 11 is a timing chart for the processing to be performed when X-rays are sensed in sensing mode 3;

DESCRIPTION OF THE EMBODIMENTS

The embodiments of the present invention will be described in detail below with reference to the accompanying drawings. Although the following embodiments will exemplify cases in which X-ray images are obtained, the effects of the present invention can also be obtained even in imaging operations using α-rays, β-rays, and γ-rays as radiations other than X-rays and other electromagnetic waves.

First Embodiment

Figure 1:
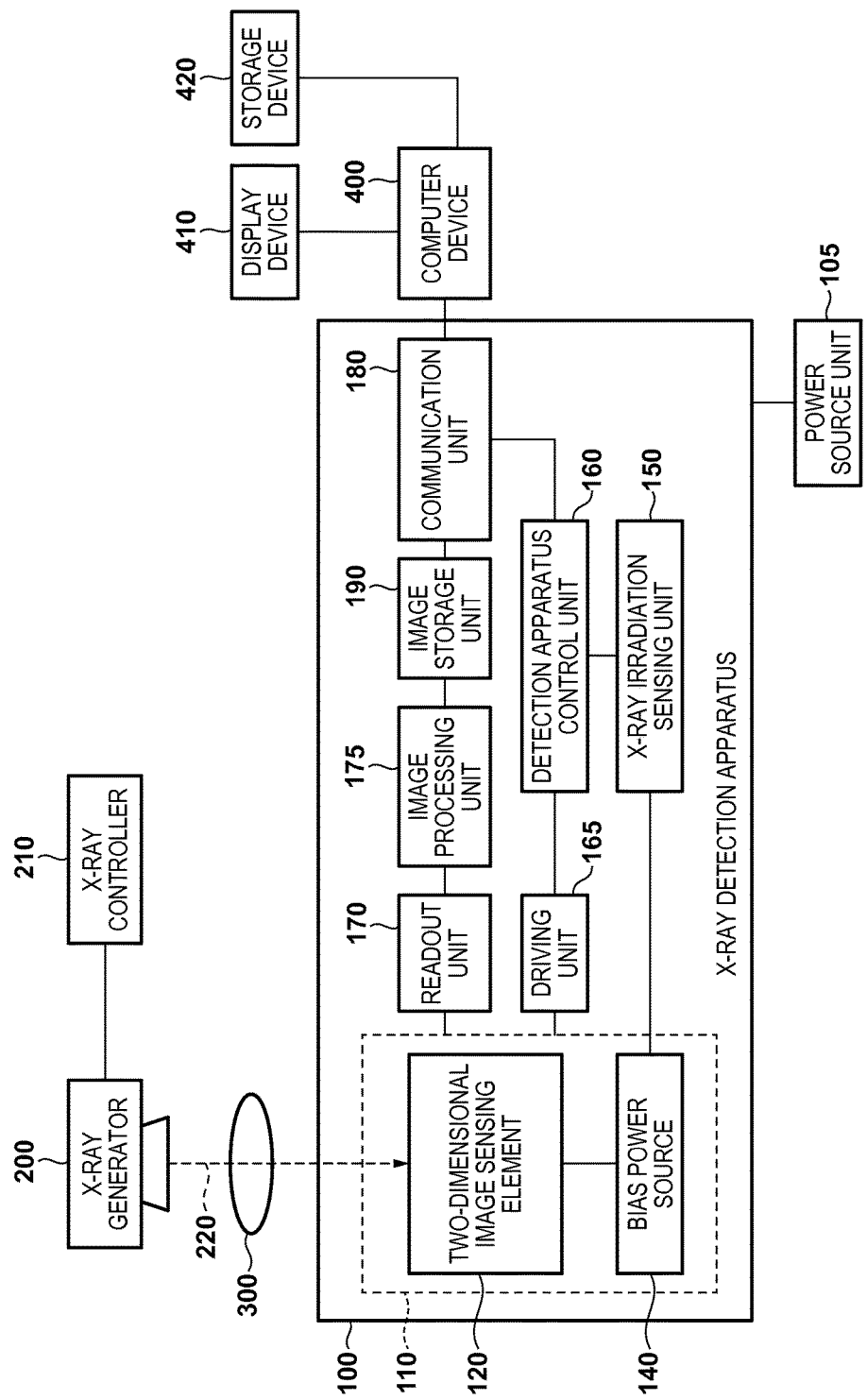
FIG. 1 is a block diagram of an X-ray imaging system according to the first embodiment.

FIG. 1 is a block diagram showing the arrangement of an X-ray imaging system 10 according to the first embodiment. The X-ray imaging system according to this embodiment includes a power source unit 105, an X-ray detection apparatus 100, an X-ray generator 200, an X-ray controller 210, a computer device 400, a display device 410, and a storage device 420. The X-ray detection apparatus 100 according to the embodiment includes an X-ray detector 110 constituted by a two-dimensional image sensing element 120 and a bias power source 140, an X-ray irradiation sensing unit 150, a control unit 160, a driving unit 165, a readout unit 170, an image processing unit 175, an image storage unit 190, and a communication unit 180.

The X-ray detection apparatus 100 includes an X-ray sensor (radiation sensor) including the two-dimensional image sensing element 120 and a scintillator. The two-dimensional image sensing element 120 is formed by arraying a plurality of solid-state photoelectric conversion elements in a two-dimensional matrix. The bias power source 140 supplies a bias voltage to the two-dimensional image sensing element 120. The X-ray irradiation sensing unit 150 (sensing circuit) is connected to the bias power source 140 and senses X-ray irradiation. The control unit 160 controls various types of operations of the X-ray detection apparatus 100. The readout unit 170 reads out image data. The image processing unit 175 processes the readout image. The communication unit 180 is a communication circuit having an antenna, and performs reception and the like of control signals transmitted from the computer device 400 for control located outside. Although the computer device 400 is assumed to be a general PC (Personal Computer), a smart device or cellular phone may be used. In some cases, an in-hospital server or cloud system may be used. In addition, in some cases, it is possible to use a system arrangement obtained by incorporating the X-ray detection apparatus 100 with a display in the computer device 400 for control.

The X-ray generator 200 generates pulse-like X-rays 220. The X-ray controller 210 controls X-ray generation conditions such as an X-ray ON/OFF operation, a tube current, and a tube voltage for the X-ray generator 200. The X-rays 220 generated by the X-ray generator 200 irradiate an object 300. The X-rays 220 transmitted through the object 300 enter the two-dimensional image sensing element 120 arranged in the X-ray detection apparatus 100. The two-dimensional image sensing element 120 converts the X-rays 220 into an X-ray image (radiation image). The X-ray image is read out by the readout unit 170 (readout circuit) and then stored in the image storage unit 190 via the image processing unit 175. The image storage unit 190 has a storage capacity large enough to store at least one image data.

The image data completely stored in the image storage unit 190 is transmitted to the outside via the communication unit 180. In this case, while the image data is stored in the image storage unit 190, the image data may be simultaneously transmitted to the outside. However, it is possible to hold all the image data in the image storage unit 190. This is because the X-ray detection apparatus 100 can retransmit the image data when, for example, part of the image data is not transmitted because of a defective communication state or the like, and an external computer device or the like cannot reproduce an accurate image. The image transmitted to the outside is stored in the storage device 420 or displayed on the display device 410. The communication unit 180 may have either a wired communication function or a wireless communication function. In addition, image data may be stored in the storage device 420 without via the computer device 400. Alternatively, the X-ray detection apparatus 100 may incorporate a storage unit (not shown) other than the image storage unit 190 and can store image data in the storage unit.

In addition, the power source unit 105 is connected to the X-ray detection apparatus 100. If the communication unit 180 has the wireless communication function, the X-ray detection apparatus 100 generally incorporates a battery as the power source unit 105. If the communication unit 180 has the wired communication function, a power source capable of wired connection is connected as the power source unit 105 to the X-ray detection apparatus 100 according to one embodiment. Note that when the communication unit 180 has the wired communication function, the X-ray detection apparatus is often used while being mounted on a standing gantry or embedded in a table according to one embodiment. The communication unit 180 sometimes has both the wireless communication function and the wired communication function. In this case, the wired communication function and the wireless communication function of the communication unit 180 are automatically switched upon being attached/detached to/from a cradle or the like, and the power source unit 105 is switched accordingly between a built-in battery and a wired power source.

Figure 2:
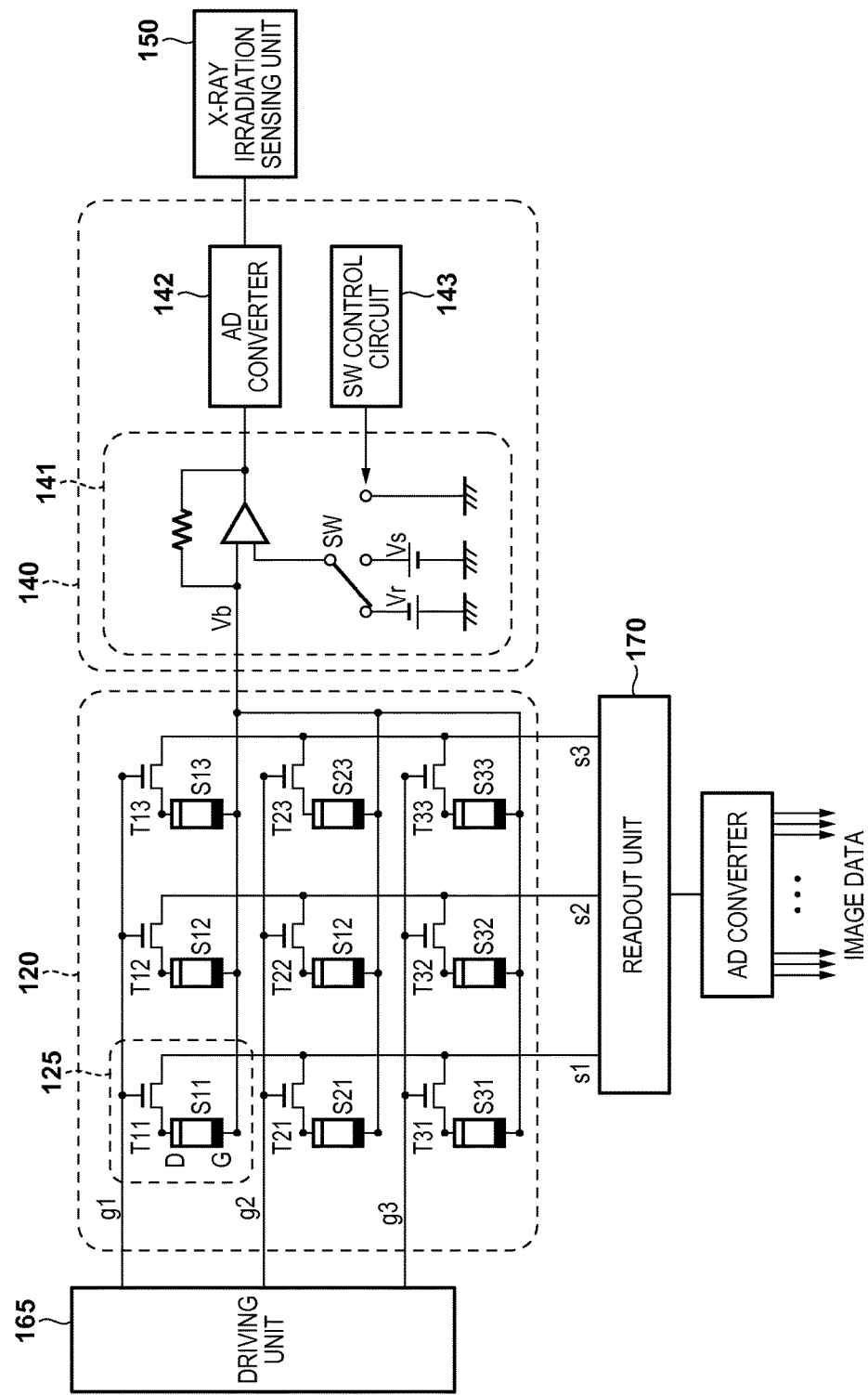
FIG. 2 is an equivalent circuit diagram of an X-ray detector according to the first embodiment.

FIG. 2 is an equivalent circuit diagram of the X-ray detector 110. The two-dimensional image sensing element 120 is constituted by a plurality of pixels arrayed in an m (row)×n (column) matrix. For the sake of descriptive simplicity, FIG. 2 shows a 3×3 matrix, with m=3 and n=3. However, an actual detection apparatus includes many pixels, for example, m=2800 and n=2800. Each pixel, as exemplified as a pixel 125, is constituted by a photoelectric conversion element S11, a phosphor (not shown) which converts the X-rays 220 into light in a wavelength band that can be sensed by the photoelectric conversion element S11, and a switch element T11.

Each photoelectric conversion element (S11 to S33) generates and accumulates charges corresponding to the incident dose of X-rays. The transmission dose of X-rays through the object 300 differs in distribution depending on through which part in the object, including structures such as bones and internal organs and focuses of disease, X-rays are transmitted. Each photoelectric conversion element (S11 to S33) converts such a distribution, which differs in this manner, into the distribution of charges and accumulates it. As each photoelectric conversion element (S11 to S33), various types of elements using amorphous silicon and polysilicon are known, as well as a CCD. In this embodiment, as each photoelectric conversion element (S11 to S33), a MIS photodiode made of amorphous silicon as a main material and arranged on an insulating substrate such as a glass substrate is used. However, a PIN photodiode may be used. In addition, a direct type conversion element which directly converts radiation into charges can be suitably used. As each switch element (T11 to T33), a transistor having a control terminal and two main terminals is suitably used. This embodiment uses a TFT (Thin-Film Transistor).

In the pixel 125, the electrode on the lower electrode side is shown as the G electrode, and the electrode on the upper electrode side is shown as the D electrode. In the pixel 125, the D electrode is electrically connected to one of the two main terminals of the switch element. On the other hand, the G electrode is connected to the bias power source 140 via a common bias wiring. When taking the first row as an example, the control terminals of the plurality of switch elements T11, T12, and T13 in the row direction are commonly connected to a driving wiring g1 on the first row, and the driving unit 165 (driving circuit) supplies a driving signal for controlling the conductive states of the switch elements T11, T12, and T13 via the driving wiring g1 for each row.

When taking the first column as an example, the main terminals of the plurality of switch elements T11, T21, and T31 in the column direction, which are not connected to the photoelectric conversion elements S11, S21, and S31, are electrically connected to a signal wiring s1 on the first column. While the switch elements T11, T21, and T31 are in the conductive state, electric signals corresponding to the charge amounts accumulated in the photoelectric conversion elements S11, S21, and S31 are output to the readout unit 170 via the signal wiring s1. A plurality of signal wirings s1 to s3 in the column direction parallelly transmit the electric signals read out from a plurality of pixels to the readout unit 170.

The readout unit 170 includes a multiplexer (not shown) which sequentially processes parallelly readout electric signals and outputs the resultant signals as a serial image signal and a buffer amplifier (not shown) which outputs the image signal after impedance conversion. An AD converter 171 converts the image signal as the analog electric signal output from the buffer amplifier into digital image data.

The bias power source 140 supplies a bias voltage Vb to the G electrode of each photoelectric conversion element (S11 to S33) via the bias wiring, and also outputs current information containing a change in current amount supplied to the bias wiring. In this embodiment, a circuit (sensing circuit) which outputs current information for sensing X-ray irradiation includes a current-voltage conversion circuit 141 constituted by an operational amplifier and a resistor and an AD converter 142 which converts a converted output voltage into a digital value. However, this is not exhaustive. For example, a current-voltage conversion circuit using a shunt resistor may be used. In addition, the bias power source 140 may directly output an output voltage from the current-voltage conversion circuit 141. Furthermore, the bias power source 140 may output a physical amount corresponding to the current amount supplied to the bias wiring.

The current information output from the bias power source 140 is sent to the X-ray irradiation sensing unit 150. This information is used to sense X-ray irradiation by capturing a change in current amount caused during X-ray irradiation. In addition, the bias power source 140 also includes a refresh voltage Vr. Like a voltage Vs, the voltage Vr is connected to the G electrode of each photoelectric conversion element (S11 to S33) via the bias wiring. The voltage Vr is applied to the G electrode during a refresh period of the photoelectric conversion element. An SW control circuit 143 controls a voltage to be applied to the G electrode. The SW control circuit 143 performs control to apply the voltage Vr during a refresh period (refresh mode period) and the voltage Vs during a period (photoelectric conversion mode period) other than the refresh period.

A method of sensing X-ray irradiation according to this embodiment will be described below. As information for sensing X-ray irradiation, the current information on the bias wiring described above can be used without any change. The X-ray irradiation sensing unit 150 can determine the start of X-ray irradiation by determining whether a sampled value of an input current exceeds a predetermined threshold. Setting a low threshold allows the X-ray irradiation sensing unit 150 to quickly sense the start of X-ray irradiation. In this case, however, the X-ray irradiation sensing unit 150 becomes susceptible to, for example, an impact or magnetic field noise and may suffer erroneous sensing (a state in which it determines the occurrence of irradiation in spite of the fact that no X-ray irradiation has occurred). In contrast to this, setting a high threshold will decrease the risk of erroneous sensing caused by noise in the X-ray irradiation sensing unit 150. However, this will delay the timing of sensing X-ray irradiation. Prolonging the time from the start of X-ray irradiation to the sensing of it will cause an artifact in an image. In consideration of this problem, the time from the start of irradiation to the determination of it can be shorter. It is possible to decide an optimal sensing threshold in consideration of these points.

In addition, the X-ray sensing sensitivity may be decreased by adjusting the bias voltage Vb to be applied (for example, setting a low bias at the time of accumulation by setting the voltage Vs to a high voltage) when detecting X-rays with low sensitivity. In this case, the standby time shortens to produce merits, such as reducing the load on each X-ray detecting element and shortening the recovery time from refresh. However, using the current information without any change will arise a problem that the sensing performance changes in accordance with the incident dose of X-rays per unit time.

Figure 3:
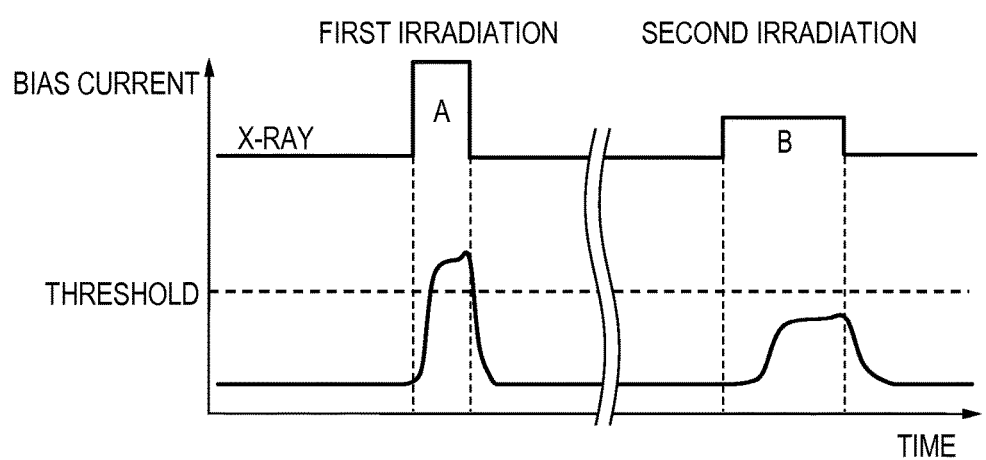
FIG. 3 is a graph schematically showing a change in current information at the time of X-ray irradiation.

FIG. 3 is a graph schematically showing the current information (bias current) output from the bias power source 140 upon X-ray irradiation. FIG. 3 shows the state of the second X-ray irradiation. Areas A and B respectively defined by the products of the irradiation time widths and the values of the bias currents in the first irradiation and the second irradiation are equal to each other, and hence there is no density difference between obtained images. That is, identical images can be obtained by the first irradiation and the second irradiation. On the other hand, the X-ray irradiation time in the first irradiation is shorter than that in the second irradiation. This is equivalent to that X-rays are output with a higher tube current in the first irradiation (assume that other imaging conditions such as a tube voltage, an object and a distance between a tube and FPD remain the same). Checking a change in bias current at this time reveals that the crest value (the value of the bias current) in the first irradiation is higher than that in the second irradiation. If, therefore, a threshold is set as indicated by the dotted line in FIG. 3, it can occur that the first irradiation is sensed because the crest value is higher than the threshold, but the second irradiation is not be sensed because the crest value is lower than the threshold. Some X-ray generator cannot generate a high tube current. A combination with such an X-ray generator may lead to the risk of failing to sense irradiation.

Figure 4:
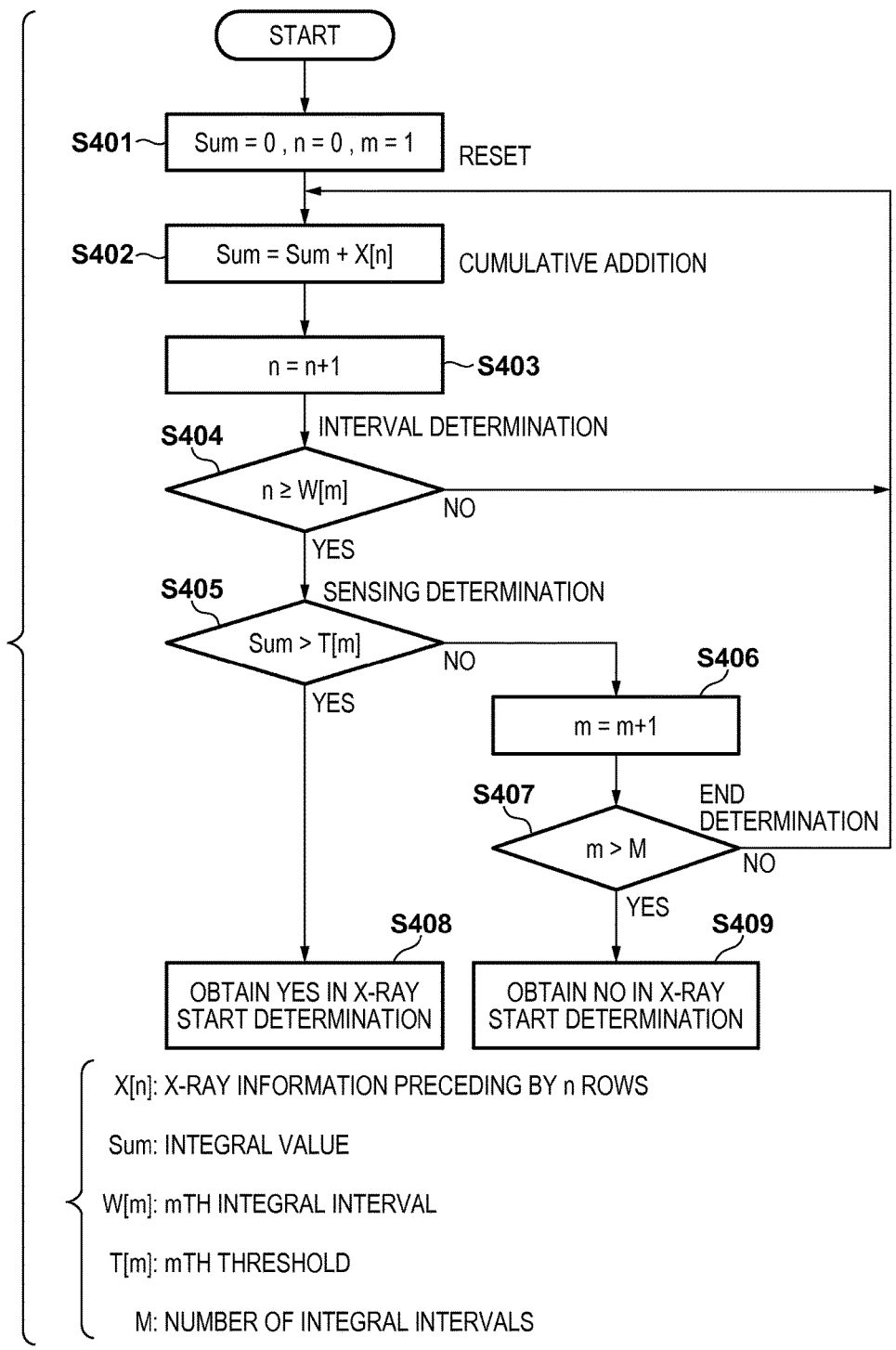
FIG. 4 is a flowchart showing the processing of determining the start of X-ray irradiation according to the first embodiment.
Figure 5:
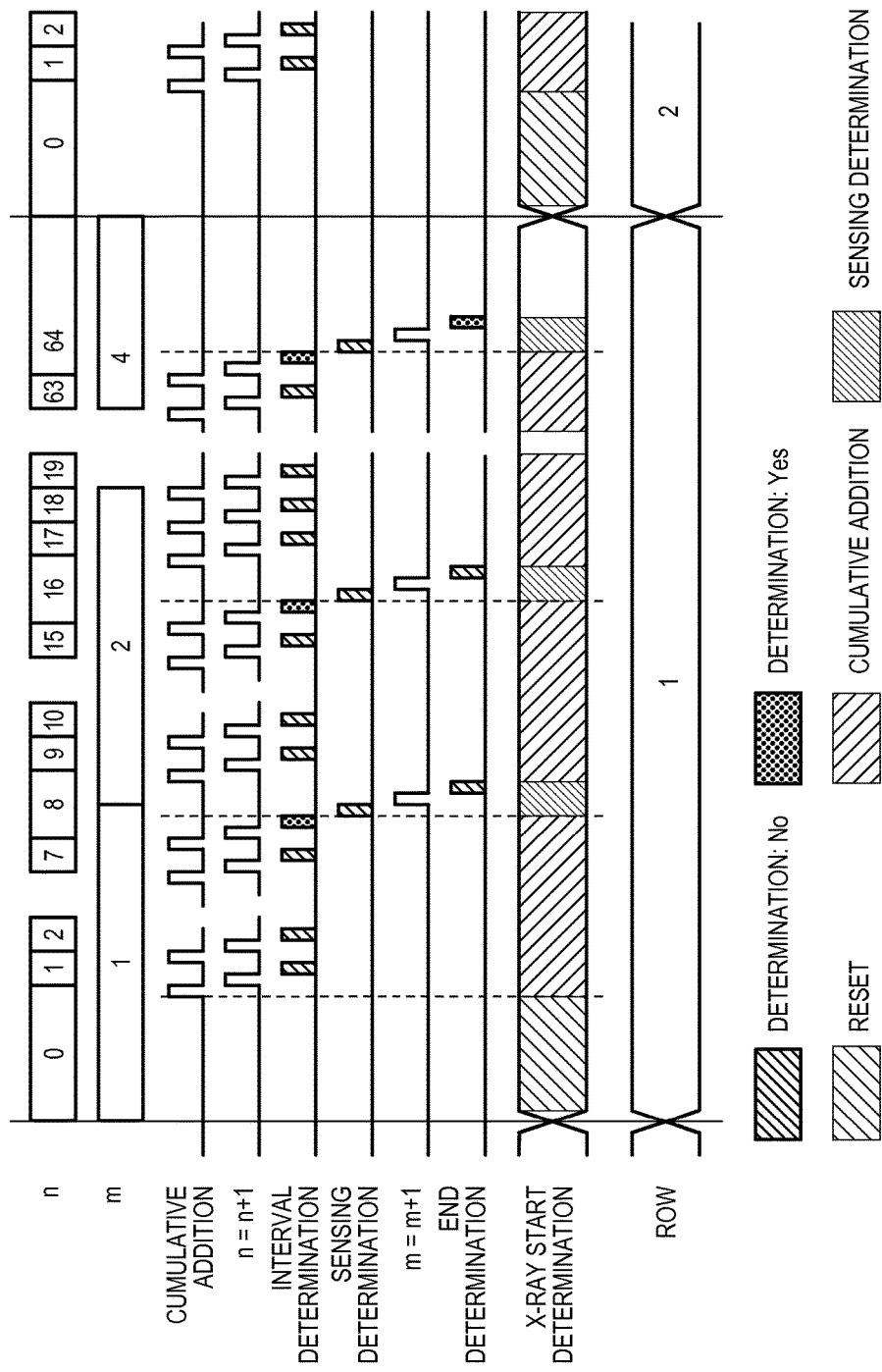
FIG. 5 is a timing chart for the processing of determining the start of X-ray irradiation according to the first embodiment.

In order to cope with such a problem, in this embodiment, the X-ray irradiation sensing unit 150 determines whether X-ray irradiation is started, by integrating values X[N] obtained by sampling current information on a bias wiring. FIG. 4 is a flowchart for the determination of the start of X-ray irradiation. FIG. 5 is a timing chart for the determination of the start of X-ray irradiation. First of all, the X-ray irradiation sensing unit 150 respectively gives the initial values to Sum representing an integral value, n representing the index of a sampled value, and m representing an integral interval number (step S401). The initial values are respectively Sum=0, n=0, and m=1. This operation will be called integrator resetting. The X-ray irradiation sensing unit 150 then sets, as the new integral value Sum, the value obtained by adding the integral value sum and X[n] representing a sampled value preceding by n values. That is, Sum=Sum+X[n] (step S402). After such cumulative addition, the X-ray irradiation sensing unit 150 sets n=n+1 (step S403), and then performs interval determination (step S404).

In the interval determination in step S404, if the index n of a sampled value does not exceed a pre-designated mth integral interval W[m] (NO in step S404), the X-ray irradiation sensing unit 150 performs cumulative addition again. If the index n of the sampled value exceeds W[m] (YES in step S404), the X-ray irradiation sensing unit 150 performs sensing determination (step S405). In the sensing determination in step S405, if the integral value Sum exceeds a pre-designated threshold T[m] in the mth interval (YES in step S405), the X-ray irradiation sensing unit 150 outputs information indicating the start of X-ray irradiation (step S408). If the integral value Sum does not exceed the threshold T[m] in the mth interval (NO in step S405), the X-ray irradiation sensing unit 150 sets m=m+1 (step S406), and performs end determination (step S407). In the end determination in step S407, if the integral interval number m does not exceed the number M of integral intervals (NO in step S407), the X-ray irradiation sensing unit 150 performs cumulative addition again. If m exceeds M (YES in step S407), the X-ray irradiation sensing unit 150 outputs X-ray information indicating that X-ray irradiation is not started (step S409).

In general, M is a value equal to or more than 1. The larger the value M, the wider the range of irradiation conditions which can be detected. Shortening the integral interval will widen a range corresponding to imaging conditions for a short irradiation time with a high output. In contrast to this, prolonging the integral interval will widen a range corresponding to imaging conditions for a long irradiation time with a low output. Since adaptive irradiation conditions differ depending on integral interval settings, the X-ray irradiation sensing unit 150 can adapt to almost all the necessary irradiation conditions by setting a plurality of integral intervals at proper intervals.

In addition, the threshold T[m] in each integral interval may be kept constant regardless of the integral interval number m or may be set to an optimal value for each integral interval. In general, it is possible to set optimal thresholds in accordance with the amounts of noise contained in current signals differing for the respective integral intervals. For example, it is possible to measure the standard deviation of noise amounts and set, as a threshold, a value of an integral multiple of the measured standard deviation.

For example, an operation to be performed when the integral interval number M is 4, first integral interval W[1]=8, second integral interval W[2]=16, third integral interval W[3]=32, and fourth integral interval W[4]=64 will be described in detail below as an example. First of all, the X-ray irradiation sensing unit 150 respectively gives the initial values to Sum representing an integral value, n representing the index of a sampled value, and m representing an integral interval number (step S401). The initial values are Sum=0, n=0, and m=1. The X-ray irradiation sensing unit 150 then sets, as the new integral value Sum, the value obtained by adding the integral value sum and X[0] representing a sampled value preceding by 0 value (step S402). That is, Sum=Sum+X[0]. After such cumulative addition, the X-ray irradiation sensing unit 150 sets the index of the sampled value to n=n+1 (step S403), and then performs interval determination (step S404). After the first cumulative addition, the index of the sampled value is n=1, and hence does not exceed first integral interval W[1]=8. That is, since NO in the interval determination, the X-ray irradiation sensing unit 150 performs cumulative addition again (NO in step S404→step S402).

After such cumulative addition is repeated eight times, the value obtained by integrating eight sampled values is stored in the integral value Sum. In addition, the index of the sampled value is n=8, and hence exceeds first integral interval W[1]=8. That is, since YES is obtained in the interval determination in step S404, the X-ray irradiation sensing unit 150 performs sensing determination (step S405). In the sensing determination, if the integral value Sum does not exceed a pre-designated threshold T[1] in the first interval, the X-ray irradiation sensing unit 150 sets the integral interval number to m=m+1 (step S406), and then performs end determination (step S407). After the first sensing detection, the integral interval number is m=1, and hence does not exceeds M=4, which represents the number of integral intervals. That is, since NO is obtained in the end determination in step S407, the X-ray irradiation sensing unit 150 performs cumulative addition again (step S402). When the X-ray irradiation sensing unit 150 repeats cumulative addition 64 times while the threshold T[m] is not exceeded in either integral interval, the integral interval number becomes m=4. As a consequence, YES is obtained in the end determination (YES in step S407). At this time, the X-ray irradiation sensing unit 150 outputs X-ray information indicating that X-ray irradiation is not started (step S409). In contrast to this, if the threshold T[m] is exceeded in the sensing determination, the X-ray irradiation sensing unit 150 outputs X-ray information indicating the start of X-ray irradiation at this time point.

The above description has exemplified the arrangement in which the X-ray detection apparatus 100 performs sensing determination in a plurality of integral intervals by using one integrator. However, M integrators may be prepared in correspondence with M integral intervals in the X-ray detection apparatus 100 to parallelly perform sensing determination by using the respective integrators. In addition, the above description has exemplified the arrangement in which the X-ray irradiation sensing unit 150 senses the start of X-ray irradiation when the threshold is exceeded in any one of the integral intervals. However, the X-ray irradiation sensing unit 150 may determine the start of X-ray irradiation when the threshold is exceeded in a plurality of integral intervals.

Figure 6:
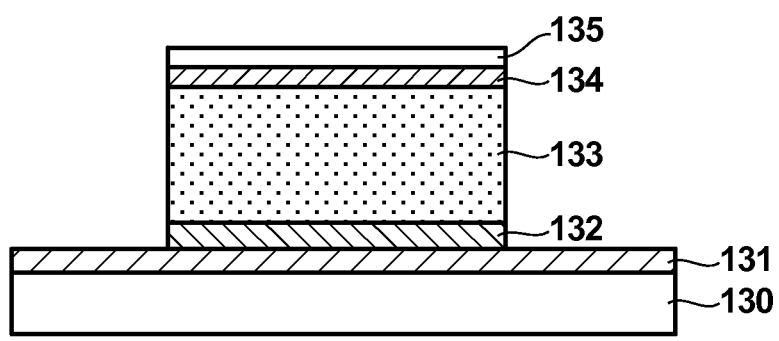
FIG. 6 is a view schematically showing the sectional structure of a photoelectric conversion element.

The operations of photoelectric conversion elements (for example, S11 to S33 in FIG. 2) will be described next. As described above, the operation modes of each photoelectric conversion element according to this embodiment include the two types, namely, the refresh mode and the photoelectric conversion mode. FIG. 6 is a view schematically showing a section of each photoelectric conversion element according to this embodiment. Various types of materials are deposited and stacked on a glass substrate 130 formed from an insulating substrate to form a photoelectric conversion element. An upper electrode 135 is formed from a transparent electrode. A lower electrode 131 is formed from Al, Cr, or the like. An insulating layer 132 is formed from an amorphous silicon nitride film to inhibit both electrons and holes. An intrinsic semiconductor layer 133 is formed from hydrogenated amorphous silicon, which generates electron-hole pairs when light enters, and operates as a photoelectric conversion layer. An impurity semiconductor layer 134 is formed from n-type amorphous silicon and operates as a hole blocking layer which blocks the injection of holes from the upper electrode 135 into the intrinsic semiconductor layer 133.

Figure 7A:
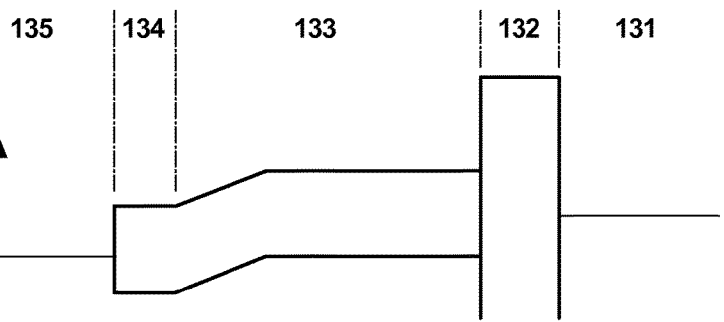
FIGS. 7A to 7D are views showing energy bands in the respective operation modes of a photoelectric conversion element.
Figure 7B:
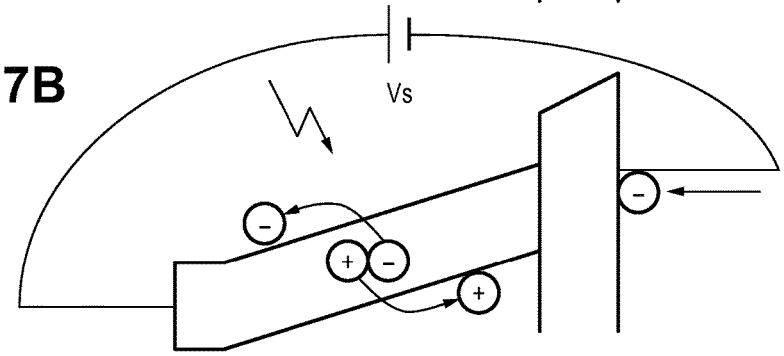
Figure 7C:
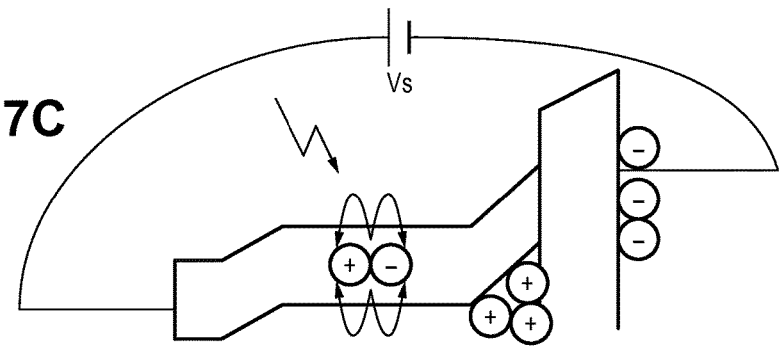
Figure 7D:
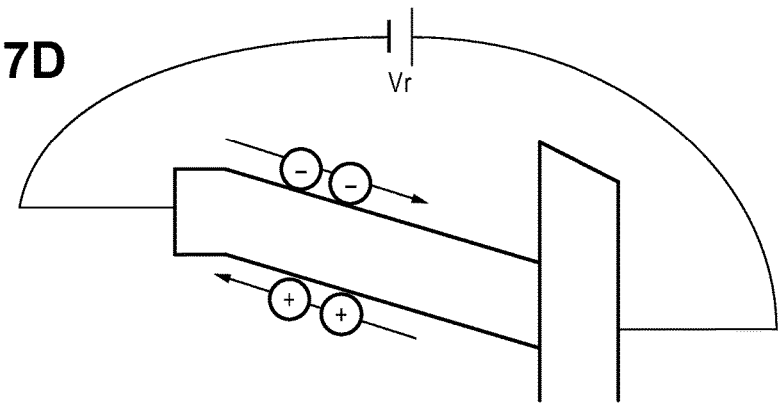

FIGS. 7A to 7D are energy band diagrams of each photoelectric conversion element. FIG. 7A shows a state without any bias. FIG. 7B shows a state in the photoelectric conversion mode. FIG. 7D shows a state in the refresh mode. In the photoelectric conversion mode in FIG. 7B, the voltage Vs as a bias voltage is applied between the upper electrode 135 and the lower electrode 131 such that a positive voltage appears on the upper electrode 135. The voltage Vs sweeps out electrons in the intrinsic semiconductor layer 133 from the upper electrode 135. On the other hand, holes are tried to be injected from the upper electrode 135 to the intrinsic semiconductor layer 133 but are blocked by the impurity semiconductor layer 134 and cannot move to the intrinsic semiconductor layer 133.

When light enters the intrinsic semiconductor layer 133 in this state, electron-hole pairs are generated by a photoelectric conversion effect. The electrons and holes move in the intrinsic semiconductor layer 133 without recombining in accordance with an electric field. The electrons are swept out from the upper electrode 135, but the holes are blocked by the insulating layer 132 and stay on its interface. When the photoelectric conversion operation continues and holes staying on the interface of the insulating layer 132 increase in number, the electric field applied to the intrinsic semiconductor layer 133 is weakened by the influence of the holes. As a result, the electron-hole pairs generated by the incident light disappear by recombination without moving by the electric field, and the photoelectric conversion element loses sensitivity to light. FIG. 7C is an energy band diagram at this time. Such a state is called saturation.

In order to make a saturated photoelectric conversion element recover sensitivity, the photoelectric conversion element needs to perform an operation called refresh. In the refresh mode of performing a refresh operation, as shown in FIG. 7D, the voltage Vr is applied between the upper electrode 135 and the lower electrode 131 such that a positive voltage appears on the lower electrode 131. In the refresh mode, holes staying on the interface of the insulating layer 132 are swept out from the upper electrode 135, and electrons are injected instead of the holes and stay on the interface of the insulating layer 132. In this case, when the photoelectric conversion element is switched again to the photoelectric conversion mode (FIG. 7B), the injected electrons are quickly swept out from the upper electrode 135, and the voltage Vs is applied as a bias voltage to make the photoelectric conversion element recover sensitivity to light.

As described above, each photoelectric conversion element needs to periodically operate in the refresh mode to maintain sensitivity to light. First of all, refresh is required immediately after light enters. This timing corresponds to a timing immediately after X-ray irradiation. That is, when an X-ray image is obtained by X-ray irradiation, each photoelectric conversion element needs to operate in the refresh mode for preparation for the next imaging operation to recover sensitivity. Even in a state without any irradiation, charges (dark current) are randomly generated in each photoelectric conversion element owing to the influences of a temperature and the like. The accumulation of charges generated randomly in this manner also makes each photoelectric conversion element gradually lose sensitivity. For this reason, when a state without irradiation continues for a predetermined time or more, each photoelectric conversion element needs to be refreshed.

Note that when a PIN photodiode or the like is used as the two-dimensional image sensing element 120, the above refresh mode itself is not required. However, an imaging recovery time shortening mode to be executed upon some kind of change in driving has a significance similar to that of the use of the refresh mode in this embodiment. Changes in driving include, for example, a change in bias including temporary bias stoppage with respect to the normal mode, a change in driving timing, and a reset operation by another light-emitting device.

Figure 8B:
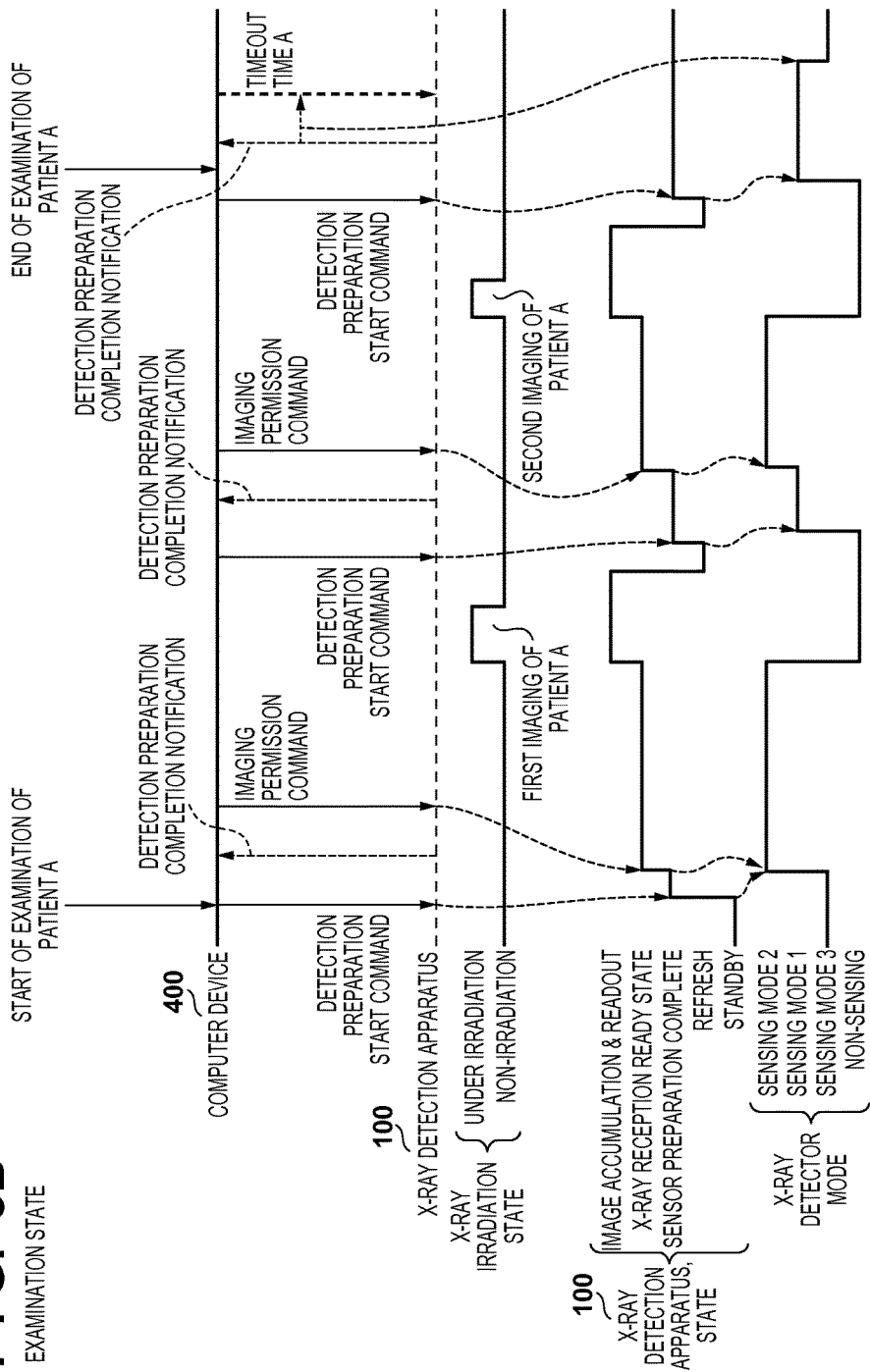

The relationship between each X-ray sensing mode of the X-ray detection apparatus and an X-ray examination state will be described next. FIGS. 8A to 8C are timing charts representing the relationships between the X-ray sensing modes and overall X-ray examination operations. FIGS. 8A to 8C show cases in which the X-ray detection apparatus 100 senses X-rays in three sensing modes. The first is sensing mode 1 corresponding to a preparation period from the end of imaging by the X-ray detection apparatus 100 to the completion of preparation for imaging. The second is sending mode 2 corresponding to an irradiation determination period from the completion of preparation for imaging to the detection of X-ray irradiation. The third is sensing mode 3 corresponding to a preparatory irradiation determination period with low possibility of X-ray irradiation after mode switching immediately after activation or in synchronism with a change in irradiation determination criterion as a trigger. The function associated with X-ray detection can be keep effective, from the viewpoint of reducing ineffective exposure. For this reason, the X-ray detection apparatus 100 detects X-rays even in a period, as a preparatory irradiation determination period, in which the possibility of X-ray irradiation is low, from the contents of instructions from the operator or information acquired by the X-ray detection apparatus 100.

In this embodiment, different thresholds for X-ray sensing are respectively set in sensing mode 1, sensing mode 2, and sensing mode 3. Letting T1 be the threshold in sensing mode 1, T2 be the threshold in sensing mode 2, and T3 be the threshold in sensing mode 3, T3>T1>T2. That is, the highest X-ray detectability is set in the period of sensing mode 2, and the lowest X-ray detectability is set in the period of sensing mode 3. Sensing mode 1 is a mode corresponding to a preparatory period in which current information is unstable. In this mode, a high threshold is set to prevent erroneous sensing caused by noise and the like. As described above, sensing mode 3 is a mode corresponding to a period with low possibility of irradiation, and hence a high threshold is set in this mode as in sensing mode 1 to prevent erroneous sensing caused by noise and the like. Note that if it is obvious that no X-ray irradiation is performed in the period of sensing mode 3, T3 may be set to infinity, that is, setting not to perform X-ray detection. In addition, the state of sensing mode 2 may be called the ON state of the function of sensing the start of irradiation, and the states of the remaining modes may be called the OFF state of the function of sensing the start of irradiation.

As shown in FIG. 8A, upon confirming that the power source is turned on, the X-ray detection apparatus 100 performs an initializing operation first. During this initialization, the sensing mode of X-ray irradiation determination is in a non-sensing state. Upon completion of the initializing operation, the sensing mode shifts to sensing mode 3 (preparatory irradiation determination period). Different conditions are set for the shift from the state after the activation to sensing mode 3 depending on the power source state for the X-ray detection apparatus 100. If, for example, the X-ray detection apparatus 100 is incorporated in a standing gantry or imaging table and always receives power from the power source unit 105, the state after the activation shifts to sensing mode 3 as soon as the completion of initialization. If the X-ray detection apparatus 100 uses an internal power source such as a battery, the state after the activation does not shift to sensing mode 3 until the reception of an explicit instruction from the operator or does not shift to sensing mode 3 at the time of the activation. Assume that the X-ray detection apparatus 100 operates on a built-in battery and is installed on the condition that no imaging is executed when it is attached to a cradle. In this case, when the X-ray detection apparatus 100 is attached to the cradle, the apparatus may stand by in a non-sensing mode, and may shift to sensing mode 3 upon detecting activity to detach the apparatus from the cradle or a vibration or impact.

When the operator inputs imaging preparation information to the computer device 400, the X-ray detection apparatus 100 receives and checks a detection preparation start command, and then immediately shifts from sensing mode 3 (preparatory irradiation determination period) to sensing mode 2 (irradiation determination period) through sensing mode 1 (preparation period). Note that when the X-ray detection apparatus 100 is not in a standby state in sensing mode 3 and receives a detection preparation start command in a non-sensing state, the apparatus shifts to sensing mode 2 after staying in sensing mode 1, for example, for a few seconds. This is because a driving state in the X-ray detection apparatus 100 in sensing mode 3 is almost the same as that in sensing mode 1, and a predetermined preparation period is required to read out an X-ray image. Note that when performing the first imaging operation upon activation of the power source, the X-ray detection apparatus 100 may shift to sensing mode 2 without being through sensing mode 1, as shown in FIG. 8A.

Upon detecting X-ray irradiation during the period of sensing mode 2, the X-ray detection apparatus 100 reads out an image and transfers it. In this period, the apparatus is set in a non-sensing state. Upon checking a detection preparation start command after performing a refresh operation, the X-ray detection apparatus 100 shifts to sensing mode 1, and then shifts to sensing mode 2 upon checking an imaging permission command.

FIG. 8B shows a case in which the X-ray detection apparatus 100 shifts to sensing mode 3 (preparatory irradiation determination period) after the end of imaging of patient A (sensing mode 1). Upon completion of the second imaging operation for this specific object (patient A), the X-ray detection apparatus 100 notifies the computer device 400 of the completion of detection preparation, and then waits for a radiation imaging permission command from the computer device 400. Assume that the X-ray detection apparatus 100 cannot confirm the reception of a radiation imaging permission command as an instruction signal within a predetermined period (timeout time A) after notification of the completion of detection preparation. In this case, the X-ray detection apparatus 100 regards that the operator has no intention to perform imaging, and then shifts to sensing mode 3 (OFF state).

In addition, as shown in FIG. 8C, upon receiving an imaging end command from the computer device 400, the X-ray detection apparatus 100 may shift to sensing mode 3 (OFF state). This imaging end command is issued when an operation input is performed to instruct the end of examination of a specific object. Upon shifting to sensing mode 3, the X-ray detection apparatus 100 operating on a built-in battery may shift from sensing mode 3 to a non-sensing state when a predetermined time (timeout time B: for example, 10 min) has elapsed after the end of the previous imaging operation to save the battery duration. In contrast to this, if there is no need to consider the battery duration or durability, the X-ray detection apparatus 100 may continue sensing mode 3. In addition, the X-ray detection apparatus 100 may return from a non-sensing state at the timing of being detached from the cradle or sensing a vibration or the like as shown in FIG. 8C as well as receiving an explicit command from the computer device 400. This is because the X-ray detection apparatus 100 regards that such an operation or the like at this timing may be one of a series of operations for imaging preparation.

FIG. 9 is a timing chart showing the driving timing of the X-ray detector 110 and indicating an operation from some midpoint in irradiation sensing driving (initial reading driving). A preparation period will be described in detail below with reference to FIG. 9. Initial reading driving is a driving operation to sequentially turn on the switch elements of the photoelectric conversion elements from the start row (y=0) to the last row (y=m), and is performed to remove charges originating from dark currents generated in the photoelectric conversion elements. Initial reading driving is repeated in a predetermined cycle until X-ray irradiation is sensed. In this period, the bias voltage Vb is always kept at the voltage Vs.

Upon X-ray irradiation, the charge amount read out by initial reading increases. At this time, the current flowing in the bias line also increases. The current information of the bias current is input to the X-ray irradiation sensing unit 150, and the start of X-ray irradiation is sensed. In this case, every time initial reading from one row is performed, integration is performed to add a sampled value X[n], and the resultant value is compared with a predetermined threshold to determine the start of irradiation. When the start of X-ray irradiation is determined, the initial reading driving is stopped at this time point (the start of X-ray irradiation is sensed on the ith row in FIG. 9), the operation shifts to the operation of accumulating charges. During the accumulation of charges, all the switch elements are OFF. When the accumulation is finished after the lapse of a predetermined time, the operation shifts to actual reading. Actual reading is performed by sequentially turning on the switch elements from the start row (y=0) to the last row (y=m).

After actual reading, refresh is immediately performed. Refresh is performed by setting the bias voltage Vb to the voltage Vr. At this time, the X-ray detector 110 may execute refresh simultaneously with respect to all the lines or sequentially. Alternatively, the X-ray detector 110 may divide the lines into several blocks and execute refresh for each block. After the refresh is finished, initial reading is started again.

During the accumulation of charges, actual reading, and refresh operation, no current signal used by the X-ray irradiation sensing unit 150 can be obtained, and hence X-ray irradiation cannot be sensed. Therefore, the X-ray irradiation sensing unit 150 is OFF. In addition, since a current signal is unstable immediately after the refresh mode is switched to the photoelectric conversion mode, the accuracy of sensing X-ray irradiation deteriorates until a current signal becomes stable. For this reason, the X-ray irradiation sensing unit 150 sometimes erroneously senses that X-ray irradiation has been performed, that is, "erroneous sensing" sometimes occurs, in spite of the fact that no X-ray irradiation has been performed. It is therefore necessary to keep the X-ray irradiation sensing unit 150 OFF for a predetermined period. If, however, X-ray irradiation is erroneously performed during a period in which the X-ray irradiation sensing unit 150 is OFF, no irradiation sensing is performed. This may cause unnecessary exposure of a patient as an object. In addition, the following problems arise.

First of all, along with irradiation, charges are generated in each photoelectric conversion element as in a normal operation. Although the generated charges are gradually removed by initial reading, charges which cannot be removed are accumulated. If imaging is performed in this state after a preparation period, the residual components of the charges generated by erroneous irradiation are superimposed on the charges generated by the imaging operation, resulting in a deterioration in the image quality of an obtained image. In addition, assume that a preparation period ends immediately after erroneous irradiation, and sensing is started. In this case, since a large amount of charges generated by erroneous irradiation stay, many charges are read out by initial reading immediately after the start of the operation of the X-ray irradiation sensing unit 150. This may make the X-ray irradiation sensing unit 150 output an image upon erroneously sensing irradiation. In this case, since imaging has not been actually performed, the image quality of the obtained image does not reach a predetermined level. It is therefore highly possible that the image cannot be properly used for diagnosis or the like. The imaging technician needs to perform, for example, misshooting processing for such images. This can increase the load on the technician.

In addition, owing to the charges generated by erroneous irradiation, the photoelectric conversion element is forced into a state like that shown in FIG. 7C. As a result, the sensitivity of the pixel itself to light deteriorates, the saturation level to incident light decreases, and the dynamic range of the image narrows. This leads to a considerable deterioration in image quality. At the same time, the sensitivity of the X-ray irradiation sensing unit 150 itself deteriorates, and hence it is not possible to accurately sense normal irradiation. This may cause the patient to repeatedly undergo ineffective exposure.

In order to minimize ineffective exposure of a patient, the X-ray detection apparatus 100 needs to sense exposure during an erroneous period and refresh each photoelectric conversion element. For this purpose, it is possible to minimize a preparation period and sense X-ray irradiation over a long period. In this embodiment, the X-ray detection apparatus 100 has a plurality of sensing modes, and uses different sensing modes in a preparation period and a sensing period, thereby sensing irradiation immediately after refresh driving.

In addition, even after the end of imaging of one patient, the X-ray detection apparatus 100 can always continue the X-ray sensing function from the viewpoint of reducing X-ray exposure as described above. On the other hand, to always continue the X-ray sensing function is to stand by while keeping the X-ray sensing function effective during a period from the end of imaging of one patient to the start of preparation for imaging of the next patient, in spite of the fact that the probability of X-ray irradiation is not high in the period. If X-ray irradiation is erroneously detected in such a period, it is necessary to perform, for example, misshooting processing. This may increase the load on the imaging technician. In such a period, therefore, it is effective to change an X-ray detection state based on a signal explicitly indicating an intention not to perform imaging in accordance with an instruction or operation from the operator while making the X-ray detection apparatus 100 continue X-ray detection.

In this case, a preparation period (a period corresponding to sensing mode 1) is a period in which a current signal for X-ray irradiation sensing after refresh and an offset component are unstable. Therefore, similar settings may be made immediately after the activation of the X-ray detection apparatus 100 as well as immediately after refresh driving. The X-ray detection apparatus 100 may arbitrarily set the length of a preparation period within a range in which image quality and the like are guaranteed, and sets the length to, for example, 10 sec. The length of a preparation period may be the same immediately after activation and immediately after refresh driving or may be individually set. In addition, the X-ray detection apparatus 100 can automatically switch to a period, as a preparation period, in which current information becomes sufficiently stable, in accordance with the state of the current information by, for example, monitoring the state of the current information using the X-ray irradiation sensing unit 150. In this case, the necessary degree of stability of current information may be arbitrarily set in consideration of image quality and the like.

FIG. 10 is a graph representing a temporal change in noise amount contained in current information. On this graph, the value of the standard deviation ($\sigma$) of noise in current information at each time point is plotted along the time axis with reference to the timing of refresh driving. Referring to FIG. 10, obviously, the noise amount rapidly decreases immediately after the refresh driving, and becomes almost stable after the lapse of a predetermined time (5 sec in FIG. 10). In this case, for example, sensing mode 1 is set in an interval from 3.3 sec to 10 sec, in which the rapid change in noise has become stable to some extent. A threshold T1 in sensing mode 1 can be set to a constant multiple of noise ($\sigma$) so as to suppress probabilistic erroneous sensing caused by a variation in noise. For example, T1=17 is set as a threshold five times a threshold five times $\sigma$ (3.4) at 3.3 sec. On the other hand, sensing mode 2 is started after the lapse of 10 sec, and T2 is set to 3.26×5=15.3.

When X-ray irradiation is sensed, image accumulation is performed regardless of the sensing mode. Upon completion of image readout operation, each element is subjected to refresh driving. The internal state of each detecting element is reset by the refresh driving to allow each element to exhibit desired performance at the time of the next imaging operation. The readout image is processed and stored in the image storage unit 190.

Note that the image obtained when X-rays are sensed in sensing mode 1 has undergone an imaging operation while an offset component is unstable, and hence may not have reached a desired image quality level. Using such an image for diagnosis may lead to a diagnostic error or oversight of a lesion. It is therefore necessary to carefully handle such an image. In addition, in sensing mode 1, since the preparation on the computer device 400 side is not made, information to be linked to an obtained image is unstable. In this case, the information to be linked to the obtained image includes information for identifying a patient, information concerning an imaging region and an imaging technique, and imaging execution information such as a tube voltage and a tube current. Lacking in such information to be managed upon being linked to an image may lead to the confusion of patient information.

Figure 12:
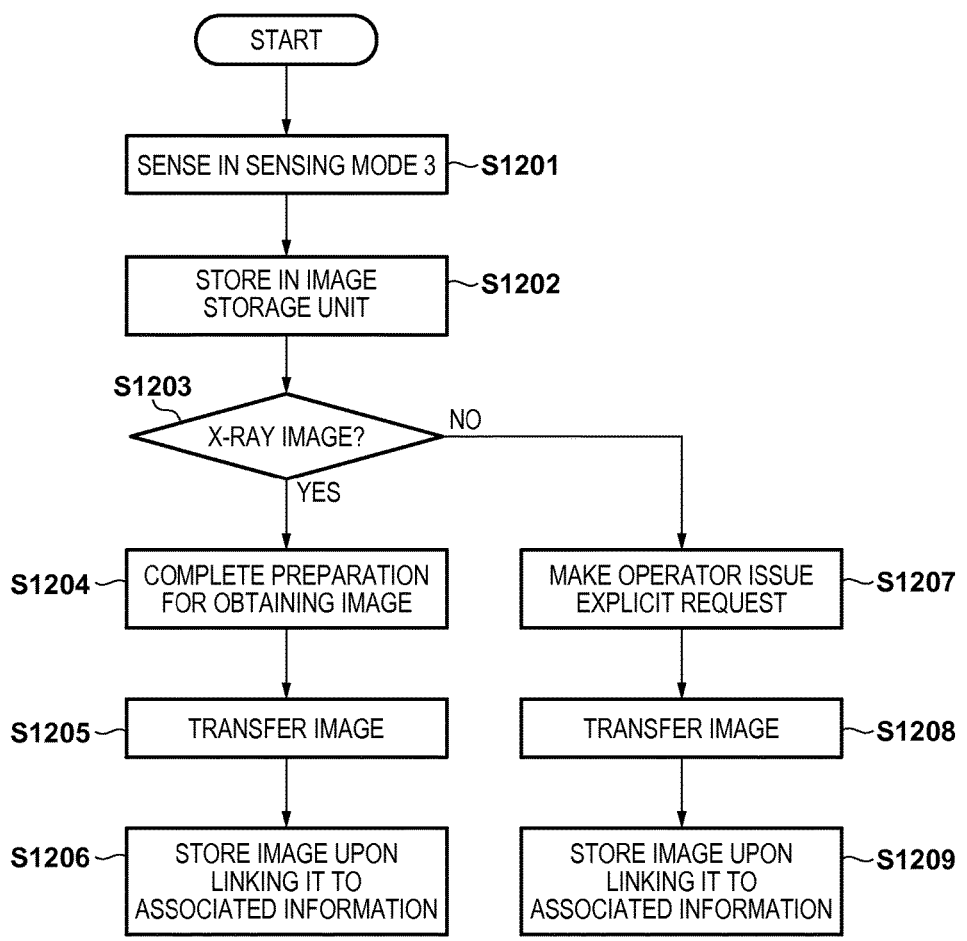
FIG. 12 is a flowchart (part 1) showing the processing to be performed when X-rays are sensed in sensing mode 3.

A case in which the X-ray detection apparatus 100 has sensed X-ray irradiation in sensing mode 3 (preparatory irradiation determination period) will be described next. FIG. 11 is a timing chart for the processing to be performed when X-ray irradiation is sensed in sending mode 3 according to this embodiment. FIG. 12 is a flowchart for the processing. Referring to FIG. 11, the X-ray detection apparatus 100 stands by in sensing mode 3 after an initializing operation upon the activation of the power source. In this case, upon detection of X-rays (imaging of a patient X in FIG. 11), the X-ray detection apparatus 100 performs image accumulation and a readout operation as described above (step S1201). Thereafter, the X-ray detection apparatus 100 temporarily stores the obtained image in the image storage unit 190 (step S1202), and determines whether the current imaging operation is actual X-ray imaging or corresponds to external magnetic field noise or vibration/impact noise (step S1203).

Figure 13A:
FIGS. 13A and 13B are graphs each exemplifying a detection waveform and vibrational noise at the time of imaging.
Figure 13B:
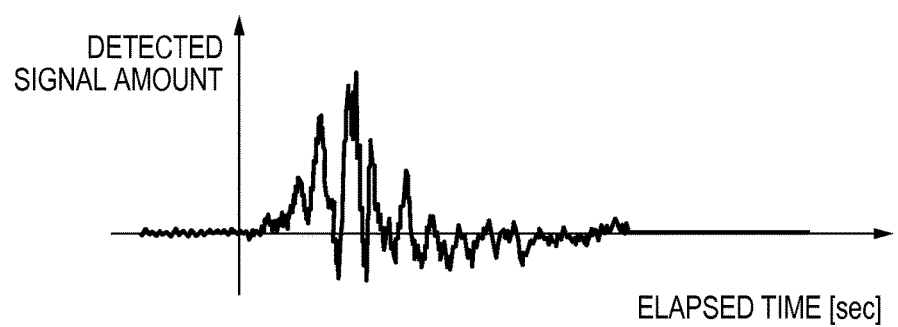

FIG. 13A shows an example of a detection waveform at the time of X-ray imaging. FIG. 13B shows an example of vibration noise. When vibration noise or external magnetic field noise is detected, a vibrational detection waveform like that shown in FIG. 13B is obtained. Therefore, the average value of such a waveform is often near to the pixel value "0", and often takes a negative value. For this reason, the image storage unit 190 handles readout data as a signed image and performs integration. If the integral value does not exceed a predetermined threshold, the image storage unit 190 determines false detection (NO in step S1203). If the integral value exceeds the threshold, the image storage unit 190 determines that the data is an X-ray image or highly likely to be the one (YES in step S1203). In this case, upon waiting for the completion of preparation for the computer device 400 (step S1204), the communication unit 180 transfers the image (step S1205). In this case, the display device 410 can actively display a message to allow the computer device 400 to select between storing the image in the storage device 420 upon linking it to information such as patient information and performing misshooting processing (step S1206).

If a detection error is determined (NO in step S1203), the display device 410 does not actively display any message to the user. The X-ray detection apparatus 100 then performs refresh and preparatory driving, and stands by in sensing mode 2→sensing mode 3 to prepare for the possibility of the next imaging operation. If the operator performs an explicit image obtaining operation (step S1207), the communication unit 180 transfers the image which has already been obtained by the X-ray detection apparatus 100 to the computer device 400 (step S1208). The computer device 400 can select between storing the image in the storage device 420 upon linking it to information such as patient information and performing misshooting processing based on an operation by the user (step S1209).

The computer device 400 may determine whether the X-ray detection apparatus 100 is ready for imaging (preparation completion state) in accordance with a communication state with the X-ray detection apparatus 100, or may switch between determining that the X-ray detection apparatus 100 is ready for imaging and determining that the X-ray detection apparatus 100 is not ready for imaging, depending on whether the user or the like has performed some kind of operation. In any case, assume that a state in which an image can be safely received immediately after imaging is an imaging ready state, and the period of an imaging ready state is regarded as an imaging ready period. In contrast to this, a period in which safe imaging cannot be performed is regarded as an imaging inhibition state, and the period of this state is regarded as an imaging inhibition period.

When the computer device 400 becomes ready for imaging, the computer device 400 notifies the X-ray detection apparatus 100 of the corresponding information. In response to this operation, the information stored in the image storage unit 190 is transferred to the computer device 400 via the communication unit 180. The computer device 400 has already received patient information to be linked to an image to be obtained next and other information, and stores the transferred image upon linking it to these pieces of information. The display device 410 displays the transferred image. If the image quality of the image is insufficient for diagnosis, the computer device 400 may discard the image by misshooting processing or the like and maintain a state in which imaging can be performed again under the same conditions.

In this case, the X-ray detection apparatus 100 may attach, to at least the image obtained by sensing X-ray irradiation in sensing mode 1, information indicating that the image has undergone irradiation during an improper period. In addition, the X-ray detection apparatus 100 may write this information in the image data as its header or store the information in a file other than the image data. Upon receiving image information attached with such information, the display device 410 may display a dialog indicating that the image has been obtained at an improper irradiation timing, together with the image, to warn the imaging technician. In addition, it is possible to make the technician to determine whether the image information is necessary, for example, to determine whether to perform misshooting processing. With these operations, the X-ray detection apparatus 100 can obtain even an X-ray image having undergone irradiation during a preparation period, and the computer device 400 can manage the image upon linking it to proper information.

As described above, according to this embodiment, the radiation detection apparatus has a plurality of sensing modes, and can perform irradiation sensing immediately after refresh driving while avoiding improper exposure by the radiation generator by setting different sensing modes in a preparation period and a sensing period, respectively. In addition, performing re-imaging processing and transfer processing as needed can store information associated with an obtained image upon linking the information to the image.

Second Embodiment

Figure 14:
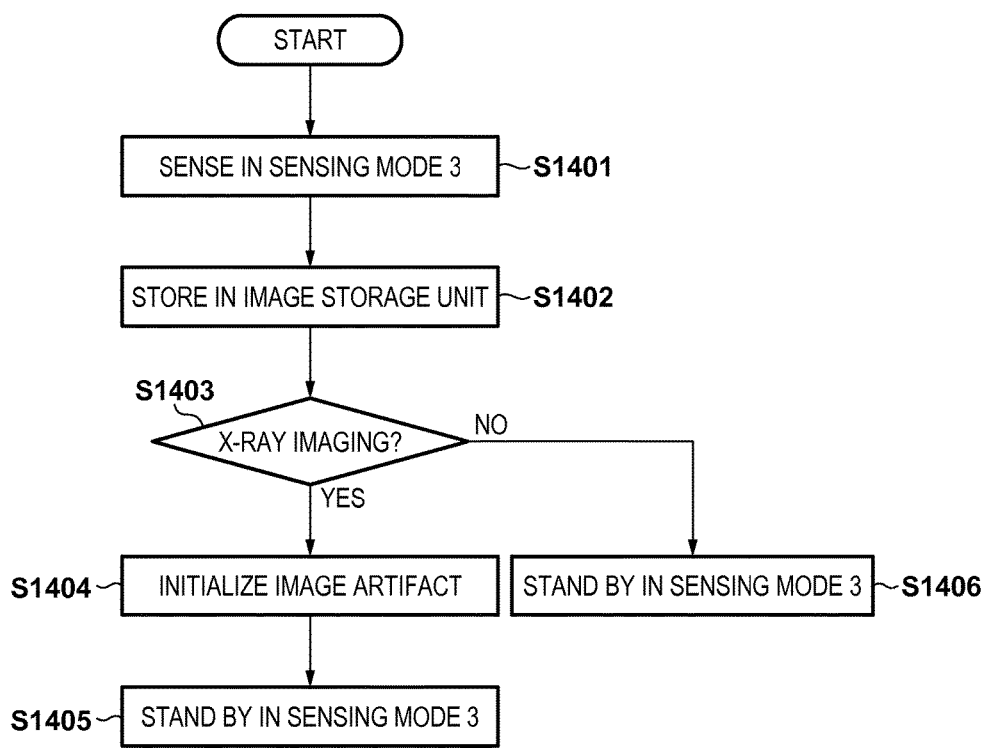
FIG. 14 is a flowchart (part 2) showing the processing to be performed when X-rays are sensed in sensing mode 3.

The second embodiment of the present invention will be described next. FIG. 14 is a flowchart showing the processing to be performed when X-rays are sensed in sensing mode 3. Processing up to the execution of sensing is the same as that in the first embodiment. In the second embodiment as well, when an X-ray irradiation sensing unit 150 determines that X-ray irradiation has been performed, and a computer device 400 becomes ready for obtaining an image, obtained image information stored in an image storage unit 190 is transferred to the computer device 400 (steps S1401 to S1403). The computer device 400 which has received the image information differs from that in the first embodiment in that it automatically processes the image as an image obtained by misshooting without storing or displaying it. Even if the computer device 400 discards the image, an X-ray detection apparatus 100 can obtain an image without any artifact by the next imaging operation upon preparing for normal imaging by performing a refresh operation (steps S1404 and S1405).

In addition, when performing misshooting processing, the computer device 400 may record information, as its reason, which indicates that the image has been obtained at an improper irradiation timing. At the same time, a display device 410 may display a dialog indicating that irradiation has been performed at an improper timing. The computer device 400 can properly manage the exposure dose for a patient by linking information such as patient information and imaging conditions to image information subjected to misshooting processing. In addition, the computer device 400 can also use the image as a diagnosis image by canceling the misshooting processing. Subsequently, the computer device 400 maintains a re-imaging enabled state with respect to the next imaging operation based on the same conditions as those for the image processed as the image obtained by misshooting. In contrast to this, if the X-ray detection apparatus 100 determines that no X-ray irradiation has been performed, the apparatus immediately returns to sensing mode 3 (preparatory irradiation determination period) and stands by without transferring any image (step S1406).

As described above, according to this embodiment, automatically processing an image as image obtained by misshooting can reduce the load on the operator and quickly prepare for the next imaging operation. This can improve the workflow.

Other Embodiments

According to other embodiments, a two-dimensional image sensing element using a PIN photoelectric conversion element may be used. In this case, it is not necessary to use a refresh power source as a power source for a voltage Vr, and initial reading in a preparation period is started without refresh after actual reading in FIG. 9. Irradiation start sensing in sensing mode 1 is started a certain time after the start of initial reading. According to the above embodiments, a current flowing in the bias power source is I/V-converted to sense the start of X-ray irradiation. However, this is not exhaustive, and an X-ray irradiation sensor for the start of irradiation other than a two-dimensional image sensing element 120 may be arranged on the X-ray incident surface side of the X-ray sensor including the two-dimensional image sensing element 120 and the scintillator to sense the irradiation of X-rays entering the X-ray sensor. The X-ray irradiation sensor is connected to a driving unit (driving circuit) 165 to transmit a signal to the driving unit 165 in accordance with the start of irradiation, thereby driving the two-dimensional image sensing element 120.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-135167, filed Jun. 30, 2014 which is hereby incorporated by reference herein in its entirety.

What is claimed is:

1. A radiation detection apparatus comprising:
   a plurality of pixels for obtaining X-ray radiation image data based on charges corresponding to X-ray radiation irradiated from a radiation generator through radiation imaging;
   a controller configured to perform controls for the radiation imaging to the plurality of pixels; and
   a sensing circuit configured to execute sensing whether or not the radiation irradiation to the plurality of pixels has been started, based on information which is obtained from the plurality of pixels and obtained separately from the radiation image,
   wherein the sensing circuit senses while changing sensing sensitivity so that the sensing sensitivity in a first period, during which the controller performs controls for the radiation imaging for obtaining X-ray radiation image data, is higher than the sensing sensitivity in a second period, during which the controller performs controls for the radiation imaging for obtaining the X-ray radiation image data, having a lower probability of the radiation irradiation than the first period, and
   wherein the controller accumulates the charges on the plurality of pixels in accordance with the sensing.

2. The apparatus according to claim 1, further comprising a bias power source that supplies a bias voltage to the plurality of pixels via bias wiring, wherein the information is based on information indicating a change in bias current flowing in the bias wiring.

3. The apparatus according to claim 2, wherein the information indicating the change in the bias current is represented by a value obtained by integrating values of the bias current with respect to a predetermined interval.

4. The apparatus according to claim 2, further comprising a communication circuit configured to, in response to transmitting a control signal from a controller that controls the radiation detection apparatus, receive the control signal from the controller,
wherein the sensing circuit switches the sensing sensitivity to first detectability upon confirming completion of preparation for the radiation imaging of the controls for the radiation imaging, and maintains the first detectability until the radiation is detected based on the radiation sensing information, the first detectability being higher than the sensing sensitivity in other periods.

5. The apparatus according to claim 4, wherein the sensing circuit switches the sensing sensitivity to second detectability upon confirming an instruction to start preparation for detection for the radiation detection apparatus based on the control signal received by the communication circuit, and maintains the second detectability until completion of preparation for the radiation imaging is confirmed, the second detectability being lower than the first detectability.

6. The apparatus according to claim 5, wherein the sensing circuit switches the sensing sensitivity to third detectability when a predetermined time has elapsed, without confirmation of completion of preparation for the radiation imaging, after switching to the second detectability, the third detectability being lower than the second detectability.

7. The apparatus according to claim 5, wherein the sensing circuit switches the sensing sensitivity to third detectability upon confirming that a power source of the radiation detection apparatus is activated, and maintains the third detectability until an instruction to start preparation for detection for the radiation detection apparatus is confirmed, the third detectability being lower than the second detectability.

8. The apparatus according to claim 5, wherein the sensing circuit switches the sensing sensitivity to third detectability upon confirming an end of imaging based on the control signal received by the communication circuit after switching to the second detectability, the third detectability being lower than the second detectability.

9. The apparatus according to claim 6, further comprising:
a storage unit configured to store image data obtained by the plurality of pixels while the sensing circuit maintains the third detectability; and
a determination unit configured to determine whether the stored image data is the X-ray radiation image data corresponding to the radiation emitted from the radiation generator,
wherein if it is determined that the image data is the X-ray radiation image data, the communication circuit transmits the image data to the controller.

10. The apparatus according to claim 9, wherein if it is determined that the image data is not the X-ray radiation image data, the communication circuit transmits the image data to the controller under a condition that an instruction is issued by a user.

11. The apparatus according to claim 5, wherein the controls for the radiation imaging comprises a preparation control which performs a preparation for the radiation imaging, a sensing control in which the sensing circuit performs the sense after an operation for the preparation is completed, a storing control which stores an electric signal corresponding to the radiation to the plurality of pixels in response to the sense indicating that the radiation irradiation to the plurality of pixels by the sensing circuit has been started, and a reading control which obtains the X-ray radiation image data based on the electric signal read from the plurality of pixels by driving the plurality of pixels, and
wherein the sensing circuit switches the sensing sensitivity so that the sensing sensitivity in the sensing control is the highest of the controls for the radiation imaging.

12. The apparatus according to claim 1, wherein the sensing circuit performs the sense by comparing the information with a threshold, the sensing sensitivity being lower in a case where the threshold is set higher and the sensing sensitivity being higher in a case where the threshold is set lower.

13. The apparatus according to claim 1, wherein the sensing circuit stops a function of the sense by changing the sensing sensitivity based on a control signal received from the controller by a communication circuit.

14. A radiation imaging apparatus comprising:
a radiation detection apparatus defined in claim 1; and
a controller configured to transmit a control signal to the radiation detection apparatus.

15. A radiation detection apparatus comprising:
a plurality of pixels for obtaining X-ray radiation image data based on charges corresponding to X-ray radiation irradiated from a radiation generator through radiation imaging;
a controller configured to perform controls for the radiation imaging to the plurality of pixels; and
a sensing circuit configured to execute sensing whether or not the radiation irradiation to the plurality of pixels has been started by comparing information, which is obtained from the plurality of pixels and obtained separately from the radiation image, with a threshold,
wherein the sensing circuit executes the sensing while changing sensing sensitivity of the sense by changing the threshold, in a period during which the controller performs controls for the radiation imaging for obtaining X-ray radiation image data, and
wherein the controller accumulates the charges on the plurality of pixels in accordance with the sensing.

16. The apparatus according to claim 15 further comprising a communication circuit configured to, in response to transmitting a control signal from a controller that controls the radiation detection apparatus, receive the control signal from the controller,
wherein when an instruction to finish an examination including at least one radiation imaging operation for a specific object is input to the controller, the sensing circuit sets the sensing sensitivity lower in accordance with reception of a control signal output by the communication circuit from the controller in accordance with an end of the examination.

17. The apparatus according to claim 15, further comprising a communication circuit configured to, in response to transmitting a control signal from a controller that controls the radiation detection apparatus, receive the control signal from the controller,
wherein when no specific object as a radiation imaging target is designated with respect to the controller, the sensing circuit sets the sensing sensitivity lower in accordance with reception of a control signal output from the controller.

18. The apparatus according claim 15, further comprising a communication circuit configured to, in response to transmitting a control signal from a controller that controls the radiation detection apparatus, receive the control signal from the controller, wherein when no instruction signal to permit imaging for an examination is received from the controller for a predetermined period, the sensing circuit sets the sensing sensitivity lower in accordance with reception of a control signal output from the controller in accordance with an end of the examination.

19. A method of controlling a radiation detection apparatus having a plurality of pixels for obtaining X-ray radiation image data based on charges corresponding to X-ray radiation irradiated from a radiation generator through radiation imaging, a controller configured to perform controls for the radiation imaging to the plurality of pixels, and a sensing circuit configured to execute sensing whether or not the radiation irradiation to the plurality of pixels has been started, based on information which is obtained from the plurality of pixels and obtained separately from the radiation image, the method comprising:

executing, by the sensing circuit, the sensing while changing sensing sensitivity of the sense so that the sensing sensitivity in a first period, in a period during which the controller performs controls for the radiation imaging for obtaining X-ray radiation image data, is higher than the sensing sensitivity in a second period, in the period during which the controller performs controls for the radiation imaging for obtaining the X-ray radiation image data, having a lower probability of the radiation irradiation than the first period; and accumulating, by the controller, the charges on the plurality of pixels in accordance with the sensing.

20. A non-transitory computer-readable storage medium storing a program for causing a computer to execute a method of controlling a radiation detection apparatus having a plurality of pixels for obtaining X-ray radiation image data based on charges corresponding to X-ray radiation irradiated from a radiation generator through radiation imaging; a controller configured to perform controls for the radiation imaging to the plurality of pixels, and a sensing circuit configured to execute sensing whether or not the radiation irradiation to the plurality of pixels has been started, based on information which is obtained from the plurality of pixels and obtained separately from the radiation image, the method comprising:

executing, by the sensing circuit, the sensing while changing sensing sensitivity of the sense so that the sensing sensitivity in a first period, in a period during which the controller performs controls for the radiation imaging for obtaining X-ray radiation image data, is higher than the sensing sensitivity in a second period, in the period during which the controller performs controls for the radiation imaging for obtaining the X-ray radiation image data, having a lower probability of the radiation irradiation than the first period; and accumulating, by the controller, the charges on the plurality of pixels in accordance with the sensing.

\* \* \* \* \*